(12) United States Patent
Abbott et al.

(10) Patent No.: US 7,662,944 B2
(45) Date of Patent: Feb. 16, 2010

(54) NUCLEIC ACID MOLECULES ENCODING PROLYL DIPEPTIDYL PEPTIDASES

(75) Inventors: Catherine Ann Abbott, Belair (AU); Mark Douglas Gorrell, Sydney (AU)

(73) Assignee: The University of Sydney, New South Wales (AU)

( * ) Notice: Subject to any disclaimer, the term of this patent is extended or adjusted under 35 U.S.C. 154(b) by 188 days.

(21) Appl. No.: 11/904,168

(22) Filed: Sep. 26, 2007

(65) Prior Publication Data
US 2008/0268532 A1 Oct. 30, 2008

Related U.S. Application Data

(62) Division of application No. 10/415,122, filed on Jun. 26, 2003, now Pat. No. 7,276,365.

(30) Foreign Application Priority Data

Oct. 27, 2000 (AU) .................................... PR1078
Oct. 29, 2001 (WO) .................... PCT/AU01/01388

(51) Int. Cl.
*C07H 21/04* (2006.01)
*C12N 9/64* (2006.01)

(52) U.S. Cl. .................................... 536/23.1; 435/226

(58) Field of Classification Search .................. None
See application file for complete search history.

(56) References Cited

FOREIGN PATENT DOCUMENTS

WO    WO 01/19866 A1    3/2001

OTHER PUBLICATIONS

Ajami et al, Dipeptidyl peptidase 9 has two forms, a broad tissue distribution, cytoplasmic localization and DPIV-like peptidase activity. Biochim Biophys Acta. Jul. 13, 2004;1679(1):18-28.*
Mentlein, Dipeptidyl-peptidase IV (CD26)—role in the inactivation of regulatory peptides. Regul Pept. Nov. 30, 1999;85(1):9-24.*
Abbott, et al., "Cloning, Expression and Chromosomal Localization of a Novel Human Dipeptidyl Peptidase (DPP) IV Homolog, DPP8", *Eur. J. Biochem.* (2000) 267:6140-6150.
GenPept AAH00970 mRNA, Partial CDS (Submitted Nov. 16, 2000), Strausberg et al, Jul. 12, 2001.

* cited by examiner

*Primary Examiner*—Sheridan Swope
(74) *Attorney, Agent, or Firm*—Husch Blackwell Sanders Welsh & Katz

(57) ABSTRACT

Peptides including HisGlyTrpSerTyrGlyGlyPheLeu; LeuAspGluAsnValHisPhePhe; GluArgHisSerIleArg and PheValIleGlnGluGluPhe which show peptidase ability and have substrate specificity for at least one of the compounds H-Ala-Pro-pNA, H-Gly-Pro-pNA and H-Arg-Pro-pNA are disclosed. Nucleic acids, vectors, antibodies and hybridoma cells are also claimed with reference to the above sequences and their abilities.

8 Claims, 14 Drawing Sheets

Figure 1

```
aagtgctaaa gcctccgagg ccaaggccgc tgctactgcc gccgctgctt cttagtgccg      60
cgttcgccgc ctgggttgtc accggcgccg ccgccgagga agccactgca accaggaccg     120
gagtggaggc ggcgcagcat gaagcggcgc aggcccgctc catagcgcac gtcgggacgg     180
tccgggcggg gccgggggga aggaaaatgc aacatggcag cagcaatgga aacagaacag     240
ctgggtgttg agatatttga aactgcggac tgtgaggaga atattgaatc acaggatcgg     300
cctaaattgg agccttttta tgttgagcgg tattcctgga gtcagcttaa aaagctgctt     360
gccgatacca gaaaatatca tggctacatg atggctaagg caccacatga tttcatgttt     420
gtgaagagga atgatccaga tggacctcat tcagacagaa tctattacct tgccatgtct     480
ggtgagaaca gagaaaatac actgttttat tctgaaattc ccaaaactat caatagagca     540
gcagtcttaa tgctctcttg gaagcctctt ttggatcttt tcaggcaac actggactat      600
ggaatgtatt ctcgagaaga agaactatta agagaaagaa aacgcattgg aacagtcgga     660
attgcttctt acgattatca ccaaggaagt ggaacatttc tgtttcaagc cggtagtgga     720
atttatcacg taaagatgg agggccacaa ggatttacgc aacaacctt aaggcccaat       780
ctagtggaaa ctagttgtcc aacatacgg atggatccaa aattatgccc cgctgatcca      840
gactggattg cttttataca tagcaacgat atttggatat ctaacatcgt aaccagagaa     900
gaaaggagac tcacttatgt gcacaatgag ctagccaaca tggaagaaga tgccagatca     960
gctggagtcg ctacctttgt tctccaagaa gaatttgata gatattctgg ctattggtgg    1020
tgtccaaaag ctgaaacaac tcccagtggt ggtaaaattc ttagaattct atatgaagaa    1080
aatgatgaat ctgaggtgga aattattcat gttacatccc ctatgttgga acaaggagg     1140
gcagattcat tccgttatcc taaaacaggt acagcaaatc ctaaagtcac ttttaagatg    1200
tcagaaataa tgattgatgc tgaaggaagg atcatagatg tcatagataa ggaactaatt    1260
caaccttttg agattctatt tgaaggagtt gaatatattg ccagagctgg atggactcct    1320
gagggaaaat atgcttggtc catcctacta gatcgctccc agactcgcct acagatagtg    1380
ttgatctcac ctgaattatt tatcccagta gaagatgatg ttatggaaag gcagagactc    1440
attgagtcag tgcctgattc tgtgacgcca ctaattatct atgaagaaac aacagacatc    1500
tggataaata tccatgacat cttttcatgtt tttccccaaa gtcacgaaga ggaaattgag    1560
tttattttg cctctgaatg caaaacaggt ttccgtcatt tatacaaat tacatctatt      1620
ttaaaggaaa gcaaatataa acgatccagt ggtgggctgc ctgctccaag tgatttcaag    1680
tgtcctatca aagaggagat agcaattacc agtggtgaat gggaagttct tggccggcat    1740
ggatctaata tccaagttga tgaagtcaga aggctggtat attttgaagg caccaaagac    1800
tccccttag agcatcacct gtacgtagtc agtacgtaa atcctggaga ggtgacaagg     1860
ctgactgacc gtggctactc acattcttgc tgcatcagtc agcactgtga cttctttata    1920
agtaagtata gtaaccagaa gaatccacac tgtgtgtccc tttacaagct atcaagtcct    1980
gaagatgacc caacttgcaa aacaaaggaa ttttgggcca ccatttggga ttcagcaggt    2040
cctcttcctg actatactcc tccagaaatt ttctctttg aaagtactac tggatttaca    2100
ttgtatggga tgctctacaa gcctcatgat ctacagcctg aaagaaata tcctactgtg    2160
ctgttcatat atggtggtcc tcaggtgcag ttggtaata atcggtttaa aggagtcaag    2220
tatttccgct tgaataccct agcctctcta ggttatgtgg ttgtagtgat agacaacagg    2280
ggatcctgtc accgagggct taaatttgaa ggcgccttta atataaaat gggtcaaata    2340
gaaattgacg atcaggtgga aggactccaa tatctagctt ctcgatatga tttcattgac    2400
ttagatcgtg tgggcatcca cggctggtcc tatggaggat acctctccct gatggcatta    2460
atgcagaggt cagatatctt cagggttgct attgctgggg ccccagtcac tctgtggatc    2520
ttctatgata caggatacac ggaacgttat atgggtcacc ctgaccagaa tgaacagggc    2580
tattacttag gatctgtggc catgcaagca gaaaagttcc cctctgaacc aaatcgttta    2640
ctgctcttac atggtttcct ggatgagaat gtccattttg cacataccag tatattactg    2700
agtttttag tgagggctgg aaagccatat gatttacaga tctatcctca ggagagacac    2760
agcataagag ttcctgaatc gggagaacat tatgaactgc atcttttgca ctaccttcaa    2820
gaaaaccttg atcacgtat tgctgctcta aagtgatat aattttgacc tgtgtagaac     2880
tctctggtat acactggcta tttaaccaaa tgaggaggtt taatcaacag aaaacacaga    2940
attgatcatc acattttgat acctgccatg taacatctac tcctgaaaat aaatgtggtg    3000
ccatgcaggg gtctacggtt tgtggtagta atctaatacc ttaaccccac atgctcaaaa    3060
tcaaatgata catattcctg agagacccag caataccata agaattacta aaaaaaaaaa    3120
```

FIG. 3a

```
            10                  30                  50
  1  CGGCGGGTCCCCTGTGTCCGCCGCGGCTGTCGTCCCCCGCTCCCGCCACTTCCGGGGTCG   60
  1   R  R  V  P  C  V  R  R  G  C  R  P  P  L  P  P  L  P  G  S   20

70                  90                 110
 61  CAGTCCGGGCATGGAGCCGCGACCGTGAGGCGCCGCTGGACCCGGGACGACCTGCCAG    120
 21   Q  S  R  A  W  S  R  D  R  E  A  P  L  D  P  G  R  P  A  Q   40

130                 150                 170
121  TCCGGCCGCCGCCCCACGTCCCGGTCTGTGTCCCACGCCTGCAGCTGGAATGGAGGCTCT  180
 41   S  G  R  R  P  T  S  R  S  V  S  H  A  C  S  W  N  G  G  S   60

190                 210                 230
181  CTGGACCCTTTAGAAGGCACCCCTGCCCTCCTGAGGTCAGCTGAGCGGTTAATGCGGAAG  240
 61   L  D  P  L  E  G  T  P  A  L  L  R  S  A  E  R  L  M  R  K   80

250                 270                 290
241  GTTAAGAAACTGCGCCTGGACAAGGAGAACACCGGAAGTTGGAGAAGCTTCTCGCTGAAT  300
 81   V  K  K  L  R  L  D  K  E  N  T  G  S  W  R  S  F  S  L  N  100

310                 330                 350
301  TCCGAGGGGGCTGAGAGGATGGCCACCACCGGGACCCCAACGGCCGACCGAGGCGACGCA  360
101   S  E  G  A  E  R  M  A  T  T  G  T  P  T  A  D  R  G  D  A  120

370                 390                 410
361  GCCGCCACAGATGACCCGGCCGCCCGCTTCCAGGTGCAGAAGCACTCGTGGGACGGGCTC  420
121   A  A  T  D  D  P  A  A  R  F  Q  V  Q  K  H  S  W  D  G  L  140

430                 450                 470
421  CGGAGCATCATCCACGGCAGCCGCAAGTACTCGGGCCTCATTGTCAACAAGGCGCCCCAC  480
141   R  S  I  I  H  G  S  R  K  Y  S  G  L  I  V  N  K  A  P  H  160

490                 510                 530
481  GACTTCCAGTTTGTGCAGAAGACGGATGAGTCTGGGCCCCACTCCCACCGCCTCTACTAC  540
161   D  F  Q  F  V  Q  K  T  D  E  S  G  P  H  S  H  R  L  Y  Y  180

550                 570                 590
541  CTGGGAATGCCATATGGCAGCCGGGAGAACTCCCTCCTCTACTCTGAGATTCCCAAGAAG  600
181   L  G  M  P  Y  G  S  R  E  N  S  L  L  Y  S  E  L  P  K  K  200

610                 630                 650
601  GTCCGGAAAGAGGCTCTGCTGCTCCTGTCCTGGAAGCAGATGCTGGATCATTTCCAGGCC  660
201   V  R  K  E  A  L  L  L  L  S  W  K  Q  M  L  D  H  F  Q  A  220

670                 690                 710
661  ACGCCCCACCATGGGGTCTACTCTCGGGAGGAGGAGCTGCTGAGGGAGCGGAAACGCCTG  720
221   T  P  H  H  G  V  Y  S  R  E  E  E  L  L  R  E  R  K  R  L  240

730                 750                 770
721  GGGGTCTTCGGCATCACCTCCTACGACTTCCACAGCGAGAGTGGCCTCTTCCTCTTCCAG  780
241   G  V  F  G  I  T  S  Y  D  F  H  S  E  S  G  L  F  L  F  Q  260

790                 810                 830
781  GCCAGCAACAGCCTCTTCCACTGCCGCGACGGCGGCAAGAACGGCTTCATGGTGTCCCCT  840
261   A  S  N  S  L  F  H  C  R  D  G  G  K  N  G  F  M  V  S  P  280

850                 870                 890
841  ATGAAACCGCTGGAAATCAAGACCCAGTGCTCAGGGCCCCGGATGGACCCCAAAATCTGC  900
281   M  K  P  L  E  I  K  T  Q  C  S  G  P  R  M  D  P  K  I  C  300
```

FIG. 3b

```
              910              930              950
 901  CCTGCCGACCCTGCCTTCTTCTCCTTCAACAATAACAGCGACCTGTGGGTGGCCAACATC  960
 301   P   A   D   P   A   F   F   S   F   N   N   N   S   D   L   W   V   A   N   I   320

970              990             1010
 961  GAGACAGGCGAGGAGCGGCGGCTGACCTTCTGCCACCAAGGTTTATCCAATGTCCTGGAT 1020
 321   E   T   G   E   E   R   R   L   T   F   C   H   Q   G   L   S   N   V   L   D   340

1030             1050             1070
1021  GACCCCAAGTCTGCGGGTGTGGCCACCTTCGTCATACAGGAAGAGTTCGACCGCTTCACT 1080
 341   D   P   K   S   A   G   V   A   T   F   V   I   Q   E   E   F   D   R   F   T   360

1090             1110             1130
1081  GGGTACTGGTGGTGCCCCACAGCCTCCTGGGAAGGTTCAGAGGGCCTCAAGACGCTGCGA 1140
 361   G   Y   W   W   C   P   T   A   S   W   E   G   S   E   G   L   K   T   L   R   380

1150             1170             1190
1141  ATCCTGTATGAGGAAGTCGATGAGTCCGAGGTGGAGGTCATTCACGTCCCCTCTCCTGCG 1200
 381   I   L   Y   E   E   V   D   E   S   E   V   E   V   I   H   V   P   S   P   A   400

1210             1230             1250
1201  CTAGAAGAAAGGAAGACGGACTCGTATCGGTACCCCAGGACAGGCAGCAAGAATCCCAAG 1260
 401   L   E   E   R   K   T   D   S   Y   R   Y   P   R   T   G   S   K   N   P   K   420

1270             1290             1310
1261  ATTGCCTTGAAAACTGGCTGAGTTCCAGACTGACAGCCAGGGCAAGATCGTCTCGACCCAG 1320
 421   I   A   L   K   L   A   E   F   Q   T   D   S   Q   G   K   I   V   S   T   Q   440

1330             1350             1370
1321  GAGAAGGAGCTGGTGCAGCCCTTCAGCTCGCTGTTCCCGAAGGTGGAGTACATCGCCAGG 1380
 441   E   K   E   L   V   Q   P   F   S   S   L   F   P   K   V   E   Y   I   A   R   460

1390             1410             1430
1381  GCCGGGTGGACCCGGGATGGCAAATACGCCTGGGCCATGTTCCTGGACCGGCCCCAGCAG 1440
 461   A   G   W   T   R   D   G   K   Y   A   W   A   M   F   L   D   R   P   Q   Q   480

1450             1470             1490
1441  TGGCTCCAGCTCGTCCTCCTCCCCCCGGCCCTGTTCATCCCGAGCACAGAGAATGAGGAG 1500
 481   W   L   Q   L   V   L   L   P   P   A   L   F   I   P   S   T   E   N   E   E   500

1510             1530             1550
1501  CAGCGGCTAGCCTCTGCCAGAGCTGTCCCCAGGAATGTCCAGCCGTATGTGGTGTACGAG 1560
 501   Q   R   L   A   S   A   R   A   V   P   R   N   V   Q   P   Y   V   V   Y   E   520

1570             1590             1610
1561  GAGGTCACCAACGTCTGGATCAATGTTCATGACATCTTCTATCCCTTCCCCCAATCAGAG 1620
 521   E   V   T   N   V   W   I   N   V   H   D   I   F   Y   P   F   P   Q   S   E   540

1630             1650             1670
1621  GGAGAGGACGAGCTCTGCTTTCTCCGCGCCAATGAATGCAAGACCGGCTTCTGCCATTTG 1680
 541   G   E   D   E   L   C   F   L   R   A   N   E   C   K   T   G   F   C   H   L   560

1690             1710             1730
1681  TACAAAGTCACCGCCGTTTTAAAAATCCCAGGGCTACGATTGGAGTGAGCCCTTCAGCCCC 1740
 561   Y   K   V   T   A   V   L   K   S   Q   G   Y   D   W   S   E   P   F   S   P   580

1750             1770             1790
1741  GGGGAAGATGAATTTAAGTGCCCCATTAAGGAAGAGATTGCTCTGACCAGCGGTGAATGG 1800
 581   G   E   D   E   F   K   C   P   I   K   E   E   I   A   L   T   S   G   E   W   600
```

FIG. 3c

```
            1810                1830                1850
1801 GAGGTTTTGGCGAGGCACGGCTCCAAGATCTGGGTCAATGAGGAGACCAAGCTGGTGTAC 1860
 601  E  V  L  A  R  H  G  S  K  I  W  V  N  E  E  T  K  L  V  Y   620

1870                1890                1910
1861 TTCCAGGGCACCAAGGACACGCCGCTGGAGCACCACCTCTACGTGGTCAGCTATGAGGCG 1920
 621  F  Q  G  T  K  D  T  P  L  E  H  H  L  Y  V  V  S  Y  E  A   640

1930                1950                1970
1921 GCCGGCGAGATCGTACGCCTCACCACGCCCGGCTTCTCCCATAGCTGCTCCATGAGCCAG 1980
 641  A  G  E  I  V  R  L  T  T  P  G  F  S  H  S  C  S  M  S  Q   660

1990                2010                2030
1981 AACTTCGACATGTTCGTCAGCCACTACAGCAGCGTGAGCACGCCGCCCTGCGTGCACGTC 2040
 661  N  F  D  M  F  V  S  H  Y  S  S  V  S  T  P  P  C  V  H  V   680

2050                2070                2090
2041 TACAAGCTGAGCGGCCCCGACGACGACCCCCTGCACAAGCAGCCCCGCTTCTGGGCTAGC 2100
 681  Y  K  L  S  G  P  D  D  D  P  L  H  K  Q  P  R  F  W  A  S   700

2110                2130                2150
2101 ATGATGGAGGCAGCCAGCTGCCCCCCGGATTATGTTCCTCCAGAGATCTTCCATTTCCAC 2160
 701  M  M  E  A  A  S  C  P  P  D  Y  V  P  P  E  I  F  H  F  H   720

2170                2190                2210
2161 ACGCGCTCGGATGTGCGGCTCTACGGCATGATCTACAAGCCCCACGCCTTGCAGCCAGGG 2220
 721  T  R  S  D  V  R  L  Y  G  M  I  Y  K  P  H  A  L  Q  P  G   740

2230                2250                2270
2221 AAGAAGCACCCCACCGTCCTCTTTGTATATGGAGGCCCCCAGGTGCAGCTGGTGAATAAC 2280
 741  K  K  H  P  T  V  L  F  V  Y  G  G  P  Q  V  Q  L  V  N  N   760

2290                2310                2330
2281 TCCTTCAAAGGCATCAAGTACTTGCGGCTCAACACACTGGCCTCCCTGGGCTACGCCGTG 2340
 761  S  F  K  G  I  K  Y  L  R  L  N  T  L  A  S  L  G  Y  A  V   780

2350                2370                2390
2341 GTTGTGATTGACGGCAGGGGCTCCTGTCAGCGAGGGCTTCGGTTCGAAGGGGCCCTGAAA 2400
 781  V  V  I  D  G  R  G  S  C  Q  R  G  L  R  F  E  G  A  L  K   800

2410                2430                2450
2401 AACCAAATGGGCCAGGTGGAGATCGAGGACCAGGTGGAGGGCCTGCAGTTCGTGGCCGAG 2460
 801  N  Q  M  G  Q  V  E  I  E  D  Q  V  E  G  L  Q  F  V  A  E   820

2470                2490                2510
2461 AAGTATGGCTTCATCGACCTGAGCCGAGTTGCCATCCATGGCTGGTCCTACGGGGGCTTC 2520
 821  K  Y  G  F  I  D  L  S  R  V  A  I  H  G  W  S  Y  G  G  F   840

2530                2550                2570
2521 CTCTCGCTCATGGGGCTAATCCACAAGCCCCAGGTGTTCAAGGTGGCCATCGCGGGTGCC 2580
 841  L  S  L  M  G  L  I  H  K  P  Q  V  F  K  V  A  I  A  G  A   860

2590                2610                2630
2581 CCGGTCACCGTCTGGATGGCCTACGACACAGGGTACACTGAGCGCTACATGGACGTCCCT 2640
 861  P  V  T  V  W  M  A  Y  D  T  G  Y  T  E  R  Y  M  D  V  P   880

2650                2670                2690
2641 GAGAACAACCAGCACGGCTATGAGGCGGGTTCCGTGGCCCTGCACGTGGAGAAGCTGCCC 2700
 881  E  N  N  Q  H  G  Y  E  A  G  S  V  A  L  H  V  E  K  L  P   900

```
2701 AATGAGCCCAACCGCTTGCTTATCCTCCACGGCTTCCTGGACGAAAACGTGCACTTTTTC 2760
 901  N  E  P  N  R  L  L  I  L  H  G  F  L  D  E  N  V  H  F  F   920

2770                2790                2810
2761 CACACAAACTTCCTCGTCTCCCAACTGATCCGAGCAGGGAAACCTTACCAGCTCCAGATC 2820
 921  H  T  N  F  L  V  S  Q  L  I  R  A  G  K  P  Y  Q  L  Q  I   940

2830                2850                2870
2821 TACCCCAACGAGAGACACAGTATTCGCTGCCCCGAGTCGGGCGAGCACTATGAAGTCACG 2880
 941  Y  P  N  E  R  H  S  I  R  C  P  E  S  G  E  H  Y  E  V  T   960

2890                2910                2930
2881 TTACTGCACTTTCTACAGGAATACCTCTGAGCCTGCCCACCGGGAGCCGCCACATCACAG 2940
 961  L  L  H  F  L  Q  E  Y  L  *

2950                2970                2990
2941 CACAAGTGGCTGCAGCCTCCGCGGGGAACCAGGCGGGAGGGACTGAGTGGCCCGCGGGCC 3000

3001 CCAGTGAGGCACTTTGTCCCGCCC  3020
```

FIG. 4

```
            SWDGL RSIIHGSRKY SGLIVNKAPH DFQFVQKTDE SGPHSHRLYY     45
                L RSIIHGSRKY SGLIVNKAPH DFQFVQKTDE SGPHSHRLYY    180

LGMPYGSREN SLLYSEIPKK VRKEALLLLS WKQHLDHFQA TPHHGVYSRE EELLRERKRL  105
LGMPYGSREN SLLYSEIPKK VRKEALLLLS WKQMLDHFQA TPHHGVYSRE EELLRERKRL  240

GVFGITSYDF HSESGLFLFQ ASNSLFHCRD GGKNGFMVSP GPGCVSPMKP LEIKTQCSGP  165
GVFGITSYDF HSESGLFLFQ ASNSLFHCRD GGKNGFM         VSPMKP LEIKTQCSGP  293

RMDPKICPAD PAFFSFINNS DLWVANIETG EERRLTFCHQ GLSNVLDDPK SAGVATFVIQ  225
RMDPKICPAD PAFFSFNNNS DLWVANIETG EERRLTFCHQ GLSNVLDDPK SAGVATFVIQ  353

EEFDRFTGYW WCPTASWE    EGLKTLRILY EEVDESEVEV IHVPSPALEE RKTDSYRYPR  283
EEFDRFTGYW WCPTASWEGS EGLKTLRILY EEVDESEVEV IHVPSPALEE RKTDSYRYPR  413

TGSKNPKIAL KLAEFQTDSQ GKIVSTQEKE LVQPFSSLFP KVEYIARAG        AWAM  336
TGSKNPKIAL KLAEFQTDSQ GKIVSTQEKE LVQPFSSLFP KVEYIARAGW TRDGKYAWAM  473

PLDRPQQWLQ LVLLPPALFI PSTENEEQRL ASARAVPRNV QPYVVYEEVT NVWINVHDIF  398
PLDRPQQWLQ LVLLPPALFI PSTENEEQRL ASARAVPRNV QPYVVYEEVT NVWINVHDIF  533

YPFPQSEGED ELCFLRANEC KTGFCHLYKV TAVLKSQGYD WSEPFSPGEG          EQ  448
YPFPQSEGED ELCFLRANEC KTGFCHLYKV TAVLKSQGYD WSEPFSPGED EFKCPIKEEI  593

SLTNA            IWVN EETKLVYFQG TKDTPLEHHL YVVSYEAAGE IVRLTTPGFS  497
ALTSGEWEVL ARHGSKIWVN EETKLVYFQG TKDTPLEHHL YVVSYEAAGE IVRLTTPGFS  653

HSCSMSQNFD MFVSHYSSVS TPPCVHVYKL SGPDDDPLHK QPRFWASMME AA          549
HSCSMSQNFD MFVSHYSSVS TPPCVHVYKL SGPDDDPLHK QPRFWASMME AASCPPDYVP  713

KIFHFHTRS DVRLYGMIYK PHALQPGKKH PTVLFVYGGP QVQLVNNSFK GIKYLRLNTL  608
PEIFHFHTRS DVRLYGMIYK PHALQPGKKH PTVLFVYGGP QVQLVNNSFK GIKYLRLNTL  773

ASLGYAVVVI DGRGSCQRGL RFEGALKNQM GQVEIEDQVE GLQFVAEKYG FIDLSRVAIH  668
ASLGYAVVVI DGRGSCQRGL RFEGALKNQM GQVEIEDQVE GLQFVAEKYG FIDLSRVAIH  833

GWSYGGFLSL MGLIHKPQVF KVAIAGAPVT VWMAYDTGYT ERYMDVPENN QHGYEAGSVA  728
GWSYGGFLSL MGLIHKPQVF KVAIAGAPVT VWMAYDTGYT ERYMDVPENN QHGYEAGSVA  893

LHVEKLPNEP NRLLILHGFL DENVHFFHTN FLVSQLIRAG KPYQLQVALP PVSPQIYPNE  788
LHVEKLPNEP NRLLILHGFL DENVHFFHTN FLVSQLIRAG KPYQL            QIYPNE  944

RHSIRCPESG EHYEVTLLHF LQEYL                                        813
RHSIRCPESG EHYEVTLLHF LQEYL                                        969
```

FIG. 5

```
RRVPCVRRGC RPPLPPLPGS QSRAWSRDRE APLDPGRPAQ SGRRPTSRSV SHACSWNGGS        60

LDPLEGTPAL LRSAERLMRK VKKLRLDKEN TGSWRSFSLN SEGAERMATT GTPTADRGDA       120
                                          P SQEPQRMC   GVSPVEQVAA

AATDDPAARF QVQKHSWDGL RSIIHGSRKY SGLIVNKAPH DFQFVQKTDE SGPHSHRLYY       180
GDMDDTAARF CVQKHSWDGL RSIIHGSRKS SGLIVSKAPH DFQFVQKPDE SGPHSHRLYY

LGMPYGSREN SLLYSEIPKK VRKEALLLLS WKQMLDHFQA TPHHGVYSRE EELLRERKRL       240
LGMPYGSREN SLLYSEIPKK VRKEALLLLS WKQMLDHFQA TPHHGVYSRE EELLRERKRL

GVFGITSYDF HSESGLFLFQ ASNSLFHCRD GGKNGFMVSP MKPLEIKTQC SGPRMDPKIC       300
GVFGITSYDF HSESGLFLFQ ASNSLFHCRD GGKNGFMVSP MKPLEIKTQC SGPRMDPKIC

PADPAFFSFN NNSDLWVANI ETGEERRLTF CHQGLSNVLD DPKSAGVATF VIQEEFDRFT       360
PADPAFFSFI NNSDLWVANI ETGEERRLTF CHQGSAGVLD NPKSAGVATF VIQEEFDRFT

GYWWCPTASW EGSEGLKTLR ILYEEVDESE VEVIHVPSPA LEERKTDSYR YPRTGSKNPK       420
GCWWCPTASW EGSEGLKTLR ILYEEVDESE VEVIHVPSPA LEERKTDSYR YPRTGSKNPK

IALKLAEFQT DSQGKIVSTQ EKELVQPFSS LFPKVEYIAR AGWTRDGKYA WAMFLDRPQQ       480
IALKLAELQT DHQGKIVSSC EKELVQPFSS LFPKVEYIAR AGWTRDGKYA WAMFLDRPQQ

WLQLVLLPPA LFIPSTENEE QRLASARAVP RNVQPYVVYE EVTNVWINVH DIFYPFPQSE       540
RLQLVLLPPA LFIPAVESEA QRQAAARAVP KNVQPFVIYE EVTNVWINVH DIFHPFPQAE

GEDELCFLRA NECKTGFCHL YKVTAVLKSQ GYDWSEPFSP GEDEFKCPIK EEIALTSGEW       600
GQQDFCFLRA NECKTGFCHL YRVTVELKTK DYDWTEPLSP TEGEFKCPIK EEVALTSGEW

EVLARHGSKI WVNEETKLVY FQGTKDTPLE HHLYVVSYEA AGEIVRLTTP GFSHSCSMSQ       660
EVLSRHGSKI WVNEQTKLVY FQGTKDTPLE HHLYVVSYES AGEIVRLTTL GFSHSCSMSQ

NFDMFVSHYS SVSTPPCVHV YKLSGPDDDP LHKQPRFWAS MMEAASCPPD YVPPEIFHFH       720
SFDMFVSHYS SVSTPPCVHV YKLSGPDDDP LHKQPRFWAS MMEAANCPPD YVPPEIFHFH

TRSDVRLYGM IYKPHALQPG KKHPTVLFVY GGPQVQLVNN SFKGIKYLRL NTLASLGYAV       780
TRADVQLYGM IYKPHTLQPG RKHPTVLFVY GGPQVQLVNN SFKGIKYLRL NTLASLGYAV

VVIDGRGSCQ RGLRFEGALK NQMGQVEIED QVEGLQFVAE KYGFIDLSRV AIHGWSYGGF       840
VVIDGRGSCQ RGLHFEGALK NQMGQVEIED QVEGLQYVAE KYGFIDLSRV AIHGWSYGGF

LSLMGLIHKP QVFKVAIAGA PVTVWMAYDT GYTERYMDVP ENNQHGYEAG SVALHVEKLP       900
LSLMGLIHKP QVFKVAIAGA PVTVWMAYDT GYTERYMDVP ENNQQGYEAG SVALHVEKLP

NEPNRLLILH GFLDENVHFF HTNFLVSQLI RAGKPYQLQI YPNERHSIRC PESGEHYEVT       960
NEPNRLLILH GFLDENVHFF HTNFLVSQLI RAGKPYQLQI YPNERHSIRC RESGEHYEVT

LLHFLQEYL                                                              969
LLHFLQEHL
```

FIG. 6a

```
GAP of: dpp9patent.dna   check: 1968   from: 1   to: 3000

/home/rpag02/Cathy/tedfamily/PATENT/dpp9patent.dna   [Unknown form]

to: mdpp9.dna   check: 672   from: 1   to: 2873

/home/rpag02/Cathy/tedfamily/PATENT/mdpp9.dna   [Unknown form]

Symbol comparison table: /dbase/gcg/gcgcore/data/rundata/nwsgapdna.cmp
CompCheck: 6876

Gap Weight:  5.000       Average Match:     1.000
      Length Weight:  0.300       Average Mismatch:  0.000

Quality: 2166.5             Length:    3172
              Ratio:  0.754               Gaps:       2
 Percent Similarity: 80.637     Percent Identity:  80.637 dpp9patent.dna x mdpp9.dna  October  5, 19101 16:00  ..

251 TGCGCCTGGACAAGGAGAACACCGGAAGTTGGAGAAGCTTCTCGCTGAAT 300
                                                      |
     1 ..............................................GCCA 4

301 TCCGAGGGGGCTGAGAGGATGGCCACCACCGGGACCCCAACGGCCGACCG 350
          ||  ||| | |  ||||||||    || ||||  | |  || |||  |
     5 TCACAGGAGCCCCAGAGGATG...TGCAGCGGGTCTCCCCAGTTGAGCA 51

351 AGGCGACGCAGCCGCCACAGATGACCCGGCCGCCCGCTTCCAGGTGCAGA 400
         | |  ||||| | ||  ||||| |||| || ||||||    |||||||
    52 GGTGGCCGCAGGGGACATGGATGACACGGCAGCACGCTTCTGTGTGCAGA 101
```

FIG. 6b

```
401 AGCACTCGTGGGACGGGCTCCGGAGCATCATCCACGGCAGCCGCAAGTAC 450
    ||||||||||||| ||||| || ||||| |||||||||| |||||| |
102 AGCACTCGTGGGATGGGCTGCGTAGCATTATCCACGGCAGTCGCAAGTCC 151

451 TCGGGCCTCATTGTCAACAAGGCGCCCCACGACTTCCAGTTTGTGCAGAA 500
    |||||||||||||| ||||| |||||||||||||||||||||||||||||
152 TCGGGCCTCATTGTCAGCAAGGCCCCCACGACTTCCAGTTTGTGCAGAA 201

501 GACGGATGAGTCTGGGCCCCACTCCCACCGCCTCTACTACCTGGGAATGC 550
    | | || |||||||| |||||||| ||||| ||||| ||||| |||||||
202 GCCTGACGAGTCTGGCCCCCACTCTCACCGTCTCTATTACCTCGGAATGC 251

551 CATATGGCAGCCGGGAGAACTCCCTCCTCTACTCTGAGATTCCCAAGAAG 600
    | || |||||||| ||||||||||||||||||| ||||| ||||||||
252 CTTACGGCAGCCGTGAGAACTCCCTCCTCTACTCCGAGATCCCCAAGAAA 301

601 GTCCGGAAAGAGGCTCTGCTGCTCCTGTCCTGGAAGCAGATGCTGGATCA 650
    || ||||| ||||| ||||||| ||||||||||||||||||||||||| ||
302 GTGCGGAAGGAGGCCCTGCTGCTGCTGTCCTGGAAGCAGATGCTGGACCA 351

651 TTTCCAGGCCACGCCCCACCATGGGGTCTACTCTCGGGAGGAGGAGCTGC 700
    |||||||||||| ||||||||||| |||||||| || ||||||||||| |
352 CTTCCAGGCCACACCCCACCATGGTGTCTACTCCCGAGAGGAGGAGCTAC 401

701 TGAGGGAGCGGAAACGCCTGGGGGTCTTCGGCATCACCTCCTACGACTTC 750
    || ||||||| || ||||||||| |||||||| |||||| || ||||||
402 TGCGGGAGCGCAAGCGCCTGGGCGTCTTCGGAATCACCTCTTATGACTTC 451

751 CACAGCGAGAGTGGCCTCTTCCTCTTCCAGGCCAGCAACAGCCTCTTCCA 800
    ||||| ||||| |||||||||||||||||||||||||||| ||||| ||||
452 CACAGTGAGAGCGGCCTCTTCCTCTTCCAGGCCAGCAATAGCCTGTTCCA 501

801 CTGCCGCGACGGCGGCAAGAACGGCTTCATGGTGTCCCCTATGAAACCGC 850
    |||| | || || |||||||| ||||| |||||||||||| ||||| || |
```

FIG. 6c

```
 502 CTGCAGGGATGGTGGCAAGAATGGCTTTATGGTGTCCCCGATGAAGCCAC  551

851 TGGAAATCAAGACCCAGTGCTCAGGGCCCCGGATGGACCCCAAAATCTGC  900
     ||||  ||||||||  |||||  ||  ||||||  ||  |||||||||||||||||||
 552 TGGAGATCAAGACTCAGTGTTCTGGCCACGCATGGACCCCAAAATCTGC  601

901 CCTGCCGACCCTGCCTTCTTCTCCTTCAACAATAACAGCGACCTGTGGGT  950
     ||  ||  ||||||||||||||  ||||||||   |||||  ||  ||||||||
 602 CCCGCAGACCCTGCCTTCTTTTCCTTCATCAACAACAGTGATCTGTGGGT  651

951 GGCCAACATCGAGACAGGCGAGGAGCGGCGGCTGACCTTCTGCCACCAAG  1000
     |||  ||||||||||||  ||  ||||||  |||||||||  ||||||||  |||||  |
 652 GGCAAACATCGAGACTGGGGAGGAACGGCGGCTCACCTTCTGTCACCAGG  701

1001 GTTTATCCAATGTCCTGGATGACCCCAAGTCTGCGGGTGTGGCCACCTTC  1050
     |||  |  |       ||||||||||  |  ||||||  ||  ||  ||  ||||||||||
 702 GTTCAGCTGGTGTCCTGGACAATCCCAAATCAGCAGGCGTGGCCACCTTT  751

1051 GTCATACAGGAAGAGTTCGACCGCTTCACTGGGTACTGGTGGTGCCCCAC  1100
     |||||  |||||  ||||||||||||||||||||||||  |||||||||||||||
 752 GTCATCCAGGAGGAGTTCGACCGCTTCACTGGGTGCTGGTGGTGCCCCAC  801

1101 AGCCTCCTGGGAAGGTTCAGAGGGCCTCAAGACGCTGCGAATCCTGTATG  1150
     |||||  ||||||||  ||  ||  ||  |||||||||||||  |||||  ||||
 802 GGCCTCTTGGGAAGGCTCCGAAGGTCTCAAGACGCTGCGCATCCTATATG  851

1151 AGGAAGTCGATGAGTCCGAGGTGGAGGTCATTCACGTCCCTCTCCTGCG  1200
     |||||||  ||  ||||||  ||  |||||||||||||  ||||||  ||  ||
 852 AGGAAGTGGACGAGTCTGAAGTGGAGGTCATTCATGTGCCTCCCCCGCC  901

1201 CTAGAAGAAAGGAAGACGGACTCGTATCGGTACCCCAGGACAGGCAGCAA  1250
     ||  ||  ||  ||||||||||||||||  ||  ||  |||||||||||||||||||||||
 902 CTGGAGGAGAGGAAGACGGACTCCTACCGCTACCCCAGGACAGGCAGCAA  951
```

Rat Multiple Tissue Northern Blot hybridised with a human DPP9 probe of 2,589 bases. The hybridisation was carried out overnight at 60° C.

Figure showing DPP9 PCR products from liver of six mice ( numbered 1 to 6) and the largest human DPP9 fragment.

NUCLEIC ACID MOLECULES ENCODING PROLYL DIPEPTIDYL PEPTIDASES

The instant application is a divisional of U.S. Ser. No. 10/415,122 filed on Jun. 26, 2003, now U.S. Pat. No. 7,276,365, which is a national stage entry of PCT/AU01/01388, International Filing Date of Oct. 29, 2001.

FIELD OF INVENTION

The invention relates to a dipeptidyl peptidase, to a nucleic acid molecule which encodes it, and to uses of the peptidase.

BACKGROUND OF THE INVENTION

The dipeptidyl peptidase (DPP) IV-like gene family is a family of molecules which have related protein structure and function [1-3]. The gene family includes the following molecules: DPPIV (CD26), dipeptidyl amino-peptidase-like protein 6 (DPP6), dipeptidyl amino-peptidase-like protein 8 (DPP8) and fibroblast activation protein (FAP) [1,2,4,5]. Another possible member is DPPIV-β [6].

The molecules of the DPPIV-like gene family are serine proteases, they are members of the peptidase family S9b, and together with prolyl endopeptidase (S9a) and acylaminoacyl peptidase (S9c), they are comprised in the prolyl oligopeptidase family[5,7].

DPPIV and FAP both have similar postproline dipeptidyl amino peptidase activity, however, unlike DPPIV, FAP also has gelatinase activity[8,9].

DPPIV substrates include chemokines such as RANTES, eotaxin, macrophage-derived chemokine and stromal-cell-derived factor 1; growth factors such as glucagon and glucagon-like peptides 1 and 2; neuropeptides including neuropeptide Y and substance P; and vasoactive peptides[10-12].

DPPIV and FAP also have non-catalytic activity; DPPIV binds adenosine deaminase, and FAP binds to α3β1, and α5β1 integrin[13-14].

In view of the above activities, the DPPIV-like family members are likely to have roles in intestinal and renal handling of proline containing peptides, cell adhesion, peptide metabolism, including metabolism of cytokines, neuropeptides, growth factors and chemokines, and immunological processes, specifically T cell stimulation[3,11,12].

Consequently, the DPPIV-like family members are likely to be involved in the pathology of disease, including for example, tumour growth and biology, type II diabetes, cirrhosis, autoimmunity, graft rejection and HIV infection[3,15-18].

Inhibitors of DPPIV have been shown to suppress arthritis, and to prolong cardiac allograft survival in animal models in vivo[19,20]. Some DPPIV inhibitors are reported to inhibit HIV infection[21]. It is anticipated that DPPIV inhibitors will be useful in other therapeutic applications including treating diarrhoea, growth hormone deficiency, lowering glucose levels in non insulin dependent diabetes mellitus and other disorders involving glucose intolerance, enhancing mucosal regeneration and as immunosuppressants[3,21-24].

There is a need to identify members of the DPPIV-like gene family as this will allow the identification of inhibitor(s) with specificity for particular family member(s), which can then be administered for the purpose of treatment of disease. Alternatively, the identified member may of itself be useful for the treatment of disease.

SUMMARY OF THE INVENTION

The present invention seeks to address the above identified need and in a first aspect provides a peptide which comprises the amino acid sequence shown in SEQ ID NO:2. As described herein, the inventors believe that the peptide is a prolyl oligopeptidase and a dipeptidyl peptidase, because it has substantial and significant homology with the amino acid sequences of DPPIV and DPP8. As homology is observed between DPP8, DPPIV and DPP9, it will be understood that DPP9 has a substrate specificity for at least one of the following compounds: H-Ala-Pro-pNA, H-Gly-Pro-pNA and H-Arg-Pro-pNA.

The peptide is homologous with human DPPIV and DPP8, and importantly, identity between the sequences of DPPIV and DPP8 and SEQ ID NO: 2 is observed at the regions of DPPIV and DPP8 containing the catalytic triad residues and the two glutamate residues of the .beta.-propeller domain essential for DPPIV enzyme activity. The observation of amino acid sequence homology means that the peptide which has the amino acid sequence shown in SEQ ID NO:2 is a member of the DPPIV-like gene family. Accordingly the peptide is now named and described herein as DPP9.

The following sequences of the human DPPIV amino acid sequence are important for the catalytic activity of DPPIV: (i) Trp$^{617}$GlyTrpSerTyrGlyGlyTyrVal, (SEQ ID NO:42); (ii) Ala$^{707}$AspAspAsnValHisPhe, (SEQ ID NO:43); (iii) Glu$^{738}$AspHisGlyIleAlaSer, (SEQ ID NO:44); (iv) Trp$^{201}$ValTyrGluGluGluVal, (SEQ ID NO:45) [25-28]. As described herein, the alignment of the following sequences of DPP9: His$^{833}$GlyTrpSerTyrGlyGlyPheLeu, (SEQ ID NO:46); Leu$^{913}$AspGluAsnValHisPhePhe, (SEQ ID NO:47); Glu$^{944}$ArgHisSerIleArg (SEQ ID NO:48) and Phe$^{350}$ValIleGlnGluGluPhe (SEQ ID NO:49) with sequences (i) to (iv) above, respectively, suggests that these sequences of DPP9 are likely to confer the catalytic activity of DPP9. This is also supported by the alignment of DPP9 and DPP8 amino acid sequences. More specifically, DPP8 has substrate specificity for H-Ala-Pro-pNA, H-Gly-Pro-pNA and H-Arg-Pro-pNA, and shares near identity, with only one position of amino acid difference, in each of the above described sequences of DPP9. Thus, in a second aspect, the invention provides a peptide comprising the following amino acid sequences: HisGlyTrpSerTyrGlyGlyPheLeu, (SEQ ID NO:50); LeuAspGluAsnValHisPhePhe, (SEQ ID NO:51); GluArgHisSerIleArg, (SEQ ID NO:52) and PheCaIleGlnGluGluPhe, (SEQ ID NO:53); which has the substrate specificity of the sequence shown in SEQ ID NO:2.

Also described herein, using the GAP sequence alignment algorithm, it is observed that DPP9 has 53% amino acid similarity and 29% amino acid identity with a C. elegans protein. Further, as shown herein, a nucleic acid molecule which encodes DPP9, is capable of hybridising specifically with DPP9 sequences derived from non-human species, including rat and mouse. Further, the inventors have isolated and characterised a mouse homologue of human DPP9. Together these data demonstrate that DPP9 is expressed in non-human species. Thus in a third aspect, the invention provides a peptide which has at least 91% amino acid identity with the amino acid sequence shown in SEQ ID NO:2, and which has the substrate specificity of the sequence shown in SEQ ID NO:2. Typically the peptide has the sequence shown in SEQ ID NO:4. Preferably, the amino acid identity is 75%.

More preferably, the amino acid identity is 95%. Amino acid identity is calculated using GAP software [GCG Version 8, Genetics Computer Group, Madison, Wis., USA] as described further herein. Typically, the peptide comprises the following sequences: HisGlyTrpSerTyrGlyGlyPheLeu, (SEQ ID NO:54); LeuAspGluAsnValHisPhePhe, (SEQ ID NO:55); GluArgHisSerIleArg, (SEQ ID NO:56); PheValIleGlnGluGLuPhe, (SEQ ID NO:57).

In view of the homology between DPPIV, DPP8 and DPP9 amino acid sequences, it is expected that these sequences will have similar tertiary structure. This means that the tertiary structure of DPP9 is likely to include the seven-blade α/β-propeller domain and the α/β hydrolase domain of DPPIV. These structures in DPP9 are likely to be conferred by the regions comprising .beta.-propeller, $Val^{226}$ to $Ala^{705}$, α/β hydrolase, $Ser^{70}$ to $Leu^{969}$ and about 70 to 90 residues in the region $Ser^{136}$ to $Gly^{225}$. As it is known that the β-propeller domain regulates proteolysis mediated by the catalytic triad in the α/β hydrolase domain of prolyl oligopeptidase, [29] it is expected that truncated forms of DPP9 can be produced, which have the substrate specificity of the sequence shown in SEQ ID NO:2, comprising the regions referred to above ($His^{833}$GlyTrpSerTyrGlyGlyPheLeu, (SEQ ID NO:46); $Leu^{913}$AspGluAsnValHisPhePhe, (SEQ ID NO:47); $Glu^{944}$ArgHisSerIleArg (SEQ ID NO:48) and $Phe^{350}$ValIleGlnGluGluPhe (SEQ ID NO:49) which confer the catalytic specificity of DPP9. Examples of truncated forms of DPP9 which might be prepared are those in which the region conferring the β-propeller domain and the α/β hydrolase domain are spliced together. Other examples of truncated forms include those that are encoded by splice variants of DPP9 mRNA. Thus although, as described herein, the biochemical characterisation of DPP9 shows that DPP9 consists of 969 amino acids and has a molecular weight of about 110 kDa, it is recognised that truncated forms of DPP9 which have the substrate specificity of the sequence shown in SEQ ID NO:2, may be prepared using standard techniques [30,31]. Thus in a fourth aspect, the invention provides a fragment of the sequence shown in SEQ ID NO: 2, which has the substrate specificity of the sequence shown in SEQ ID NO:2. The inventors believe that a fragment from Ser136 to Leu969 (numbered according to SEQ ID NO:2) would have enzyme activity.

It is recognised that DPP9 may be fused, or in other words, linked to a further amino acid sequence, to form a fusion protein which has the substrate specificity of the sequence shown in SEQ ID NO:2. An example of a fusion protein is one which comprises the sequence shown in SEQ ID NO:2 which is linked to a further amino acid sequence: a "tag" sequence which consists of an amino acid sequence encoding the V5 epitope and a His tag. An example of another further amino acid sequence which may be linked with DPP9 is a glutathione S transferase (GST) domain [30]. Another example of a further amino acid sequence is a portion of CD8.alpha. [8]. Thus in one aspect, the invention provides a fusion protein comprising the amino acid sequence shown in SEQ ID NO:2 linked with a further amino acid sequence, the fusion protein having the substrate specificity of the sequence shown in SEQ ID NO:2.

It is also recognised that the peptide of the first aspect of the invention may be comprised in a polypeptide, so that the polypeptide has the substrate specificity of DPP9. The polypeptide may be useful, for example, for altering the protease susceptibility of DPP9, when used in in vivo applications. An example of a polypeptide which may be useful in this regard, is albumin. Thus in another embodiment, the peptide of the first aspect is comprised in a polypeptide which has the substrate specificity of DPP9.

In one aspect, the invention provides a peptide which includes the amino acid sequence shown in SEQ ID NO:7. In one embodiment the peptide consists of the amino acid sequence shown in SEQ ID NO:7.

As described further herein, the amino acid sequence shown in SEQ ID NO:7, and the amino acid sequences of DPPIV, DPP8 and FAP are homologous. DPPIV, DPP8 and FAP have dipeptidyl peptidase enzymatic activity and have substrate specificity for peptides which contain the di-peptide sequence, Ala-Pro. The inventors note that the amino acid sequence shown in SEQ ID NO:7 contains the catalytic triad, Ser-Asp-His. Accordingly, it is anticipated that the amino acid sequence shown in SEQ ID NO:7 has enzymatic activity in being capable of cleaving a peptide which contains Ala-Pro by hydrolysis of a peptide bond located C-terminal adjacent to proline in the di-peptide sequence.

In one embodiment, the peptide comprises an amino acid sequence shown in SEQ ID NO:7 which is capable of cleaving a peptide bond which is C-terminal adjacent to proline in the sequence Ala-Pro. The capacity of a dipeptidyl peptidase to cleave a peptide bond which is C-terminal adjacent to proline in the di-peptide sequence Ala-Pro can be determined by standard techniques, for example, by observing hydrolysis of a peptide bond which is C-terminal adjacent to proline in the molecule Ala-Pro-p-nitroanilide.

The inventors recognise that by using standard techniques it is possible to generate a peptide which is a truncated form of the sequence shown in SEQ ID NO:7, which retains the proposed enzymatic activity described above. An example of a truncated form of the amino acid sequence shown in SEQ ID NO:7 which retains the proposed enzymatic activity is a form which includes the catalytic triad, Ser-Asp-His. Thus a truncated form may consist of less than the 831 amino acids shown in SEQ ID NO:7. Accordingly, in a further embodiment, the peptide is a truncated form of the peptide shown in SEQ ID NO:7, which is capable of cleaving a peptide bond which is C-terminal adjacent to proline in the sequence Ala-Pro.

It will be understood that the amino acid sequence shown in SEQ ID NO:7 may be altered by one or more amino acid deletions, substitutions or insertions of that amino acid sequence and yet retain the proposed enzymatic activity described above. It is expected that a peptide which is at least 47% similar to the amino acid sequence of SEQ ID NO:7, or which is at least 27% identical to the amino acid sequence of SEQ ID NO:7, will retain the proposed enzymatic activity described above. The % similarity can be determined by use of the program/algorithm "GAP" which is available from Genetics Computer Group (GCG), Wisconsin. Thus in another embodiment of the first aspect, the peptide has an amino acid sequence which is at least 47% similar to the amino acid sequence shown in SEQ ID NO:7, and is capable of cleaving a peptide bond which is C-terminal adjacent to proline in the sequence Ala-Pro.

As described above, the isolation and characterisation of DPP9 is necessary for identifying inhibitors of DPP9 catalytic activity, which may be useful for the treatment of disease. Accordingly, in a fifth aspect, the invention provides a method of identifying a molecule capable of inhibiting cleavage of a substrate by DPP9, the method comprising the following steps:

(a) contacting DPP9 with the molecule;
(b) contacting DPP9 of step (a) with a substrate capable of being cleaved by DPP9, in conditions sufficient for cleavage of the substrate by DPP9; and (c) detecting substrate not cleaved by DPP9, to identify that the molecule is capable of inhibiting cleavage of the substrate by DPP9.

It is recognised that although inhibitors of DPP9 may also inhibit DPPIV and other serine proteases, as described herein, the alignment of the DPP9 amino acid sequence with most closely related molecules, (i.e. DPPIV), reveals that the DPP9 amino acid is distinctive, particularly at the regions controlling substrate specificity. Accordingly, it is expected that it will be possible to identify inhibitors which inhibit DPP9 catalytic activity specifically, which do not inhibit catalytic activity of DPPIV-like gene family members, or other serine proteases. Thus, in a sixth aspect, the invention provides a method of identifying a molecule capable of inhibiting specifically, the cleavage of a substrate by DPP9, the method comprising the following steps:

(a) contacting DPP9 and a further protease with the molecule;
(b) contacting DPP9 and the further protease of step (a) with a substrate capable of being cleaved by DPP9 and the further protease, in conditions sufficient for cleavage of the substrate by DPP9 and the further protease; and
(c) detecting substrate not cleaved by DPP9, but cleaved by the further protease, to identify that the molecule is capable of inhibiting specifically, the cleavage of the substrate by DPP9.

In a seventh aspect, the invention provides a method of reducing or inhibiting the catalytic activity of DPP9, the method comprising the step of contacting DPP9 with an inhibitor of DPP9 catalytic activity. In view of the homology between DPP9 and DPP8 amino acid sequences, it will be understood that inhibitors of DPPB activity may be useful for inhibiting DPP9 catalytic activity. Examples of inhibitors suitable for use in the seventh aspect are described in [21,32,33]. Other inhibitors useful for inhibiting DPP9 catalytic activity can be identified by the methods of the fifth or sixth aspects of the invention.

In one embodiment, the catalytic activity of DPP9 is reduced or inhibited in a mammal by administering the inhibitor of DPP9 catalytic activity to the mammal. It is recognised that these inhibitors have been used to reduce or inhibit DPPIV catalytic activity in vivo, and therefore, may also be used for inhibiting DPP9 catalytic activity in vivo. Examples of inhibitors useful for this purpose are disclosed in the following [21,32-34].

Preferably, the catalytic activity of DPP9 in a mammal is reduced or inhibited in the mammal, for the purpose of treating a disease in the mammal. Diseases which are likely to be treated by an inhibitor of DPP9 catalytic activity are those in which DPPIV-like gene family members are associated [3,10,11,17,21,36], including for example, neoplasia, type II diabetes, cirrhosis, autoimmunity, graft rejection and HIV infection.

Preferably, the inhibitor for use in the seventh aspect of the invention is one which inhibits the cleavage of a peptide bond C-terminal adjacent to proline. As described herein, examples of these inhibitors are 4-(2-aminoethyl)benzenesulfonylfluoride, aprotinin, benzamidine/HCl, Ala-Pro-Gly, H-Lys-Pro-OH HCl salt and zinc ions, for example, zinc sulfate or zinc chloride. More preferably, the inhibitor is one which specifically inhibits DPP9 catalytic activity, and which does not inhibit the catalytic activity of other serine proteases, including, for example DPPIV, DPP8 or FAP.

In an eighth aspect, the invention provides a method of cleaving a substrate which comprises contacting the substrate with DPP9 in conditions sufficient for cleavage of the substrate by DPP9, to cleave the substrate. Examples of molecules which can be cleaved by the method are H-Ala-Pro-pNA, H-Gly-Pro-pNA and H-Arg-Pro-pNA. Molecules which are cleaved by DPPIV including RANTES, eotaxin, macrophage-derived chemokine, stromal-cell-derived factor 1, glucagon and glucagon-like peptides 1 and 2, neuropeptide Y, substance P and vasoactive peptide are also likely to be cleaved by DPP9 [11,12]. In one embodiment, the substrate is cleaved by cleaving a peptide bond C-terminal adjacent to proline in the substrate. The molecules cleaved by DPP9 may have Ala, or Trp, Ser, Gly, Val or Leu in the P1 position, in place of Pro [11,12].

The inventors have characterised the sequence of a nucleic acid molecule which encodes the amino acid sequence shown in SEQ ID NO:2. Thus in a tenth aspect, the invention provides a nucleic acid molecule which encodes the amino acid sequence shown in SEQ ID NO:2.

In an eleventh aspect, the invention provides a nucleic acid molecule which consists of the sequence shown in SEQ ID NO:1.

In another aspect, the invention provides a nucleic acid molecule which encodes a peptide comprising the amino acid sequence shown in SEQ ID NO:7.

The inventors have characterised the nucleotide sequence of the nucleic acid molecule encoding SEQ ID NO:7. The nucleotide sequence of the nucleic acid molecule encoding DPP4-like-2 is shown in SEQ ID NO:8. Thus, in one embodiment, the nucleic acid molecule comprises the nucleotide sequence shown in SEQ ID NO:8. In another embodiment, the nucleic acid molecule consists of the nucleotide sequence shown in SEQ ID NO:8.

The inventors recognise that a nucleic acid molecule which has the nucleotide sequence shown in SEQ ID NO:8 could be made by producing only the fragment of the nucleotide sequence which is translated. Thus in an embodiment, the nucleic acid molecule does not contain 5' or 3' untranslated nucleotide sequences.

As described herein, the inventors observed RNA of 4.4 kb and a minor band of 4.8 kb in length which hybridised to a nucleic acid molecule comprising sequence shown in SEQ ID NO:8. It is possible that these mRNA species are splice variants. Thus in another embodiment, the nucleic acid molecule comprises the nucleotide sequence shown in SEQ ID NO:8 and which is approximately 4.4 kb or 4.8 kb in length.

In another embodiment, the nucleic acid molecule is selected from the group of nucleic acid molecules consisting of DPP4-like-2a, DPP4-like-2b and DPP4-like-2c, as shown in FIG. 2.

In another aspect, the invention provides a nucleic acid molecule having a sequence shown in SEQ ID NO: 3.

In a twelfth aspect, the invention provides a nucleic acid molecule which is capable of hybridising to a nucleic acid molecule consisting of the sequence shown in SEQ ID NO:1 in stringent conditions, and which encodes a peptide which has the substrate specificity of the sequence shown in SEQ ID NO:2. As shown in the Northern blot analysis described herein, DPP9 mRNA hybridises specifically to the sequence shown in SEQ ID NO:1, after washing in 2.times.SSC/1.0% SDS at 37° C., or after washing in 0.1.times.SSC/0.1% SDS at 50° C. "Stringent conditions" are conditions in which the nucleic acid molecule is exposed to 2.times.SSC/1.0% SDS. Preferably, the nucleic acid molecule is capable of hybridising to a molecule consisting of the sequence shown in SEQ ID NO:1 in high stringent conditions. "High stringent conditions" are conditions in which the nucleic acid molecule is exposed to 0.1.times.SSC/0.1% SDS at 50° C.

As described herein, the inventors believe that the gene which encodes DPP9 is located at band p13.3 on human chromosome 19. The location of the DPP9 gene is distinguished from genes encoding other prolyl oligopeptidases, which are located on chromosome 2, at bands 2q24.3 and 2q23, chromosome 7 or chromosome 15q22. Thus in an embodiment, the nucleic acid molecule is one capable of hybridising to a gene which is located at band p13.3 on human chromosome 19.

It is recognised that a nucleic acid molecule which encodes the amino acid sequence shown in SEQ ID NO:2, or which comprises the sequence shown in SEQ ID NO:1, could be made by producing the fragment of the sequence which is translated, using standard techniques [30,31]. Thus in an embodiment, the nucleic acid molecule does not contain 5' or 3' untranslated sequences.

In a thirteenth aspect, the invention provides a vector which comprises a nucleic acid molecule of the tenth aspect of the invention. In one embodiment, the vector is capable of replication in a COS-7 cell, CHO cell or 293T cell, or E. coli. In another embodiment, the vector is selected from the group consisting of λTripleEx, pTripleEx, pGEM-T Easy Vector, pSecTag2Hygro, pet15b, pEE14.HCMV.gs and pCDNA3.1/V5/His.

In a fourteenth aspect, the invention provides a cell which comprises a vector of the thirteenth aspect of the invention. In one embodiment, the cell is an E. coli cell. Preferably, the E. coli is MC1061, DH5α, JM109, BL21DE3, pLysS. In another embodiment, the cell is a COS-7, COS-1, 293T or CHO cell.

In a fifteenth aspect, the invention provides a method for making a peptide of the first aspect of the invention comprising, maintaining a cell according to the fourteenth aspect of the invention in conditions sufficient for expression of the peptide by the cell. The conditions sufficient for expression are described herein. In one embodiment, the method comprises the further step of isolating the peptide.

In a sixteenth aspect, the invention provides a peptide when produced by the method of the fifteenth aspect.

In a seventeenth aspect, the invention provides a composition comprising a peptide of the first aspect and a pharmaceutically acceptable carrier.

In an eighteenth aspect, the invention provides an antibody which is capable of binding a peptide according to the first aspect of the invention. The antibody can be prepared by immunising a subject with purified DPP9 or a fragment thereof according to standard techniques [35]. An antibody may be prepared by immunising with transiently transfected DPP9+ cells. It is recognised that the antibody is useful for inhibiting activity of DPP9. In one embodiment, the antibody of the eighteenth aspect of the invention is produced by a hybridoma cell.

In a nineteenth aspect, the invention provides a hybridoma cell which secretes an antibody of the nineteenth aspect.

BRIEF DESCRIPTION OF THE FIGURES

FIG. 1. Nucleotide sequence of DPP8 (SEQ ID NO:5).

FIG. 3. Nucleotide sequence of human cDNA DPP9 (SEQ ID NO:1) and amino acid sequence of human DPP9 (SEQ ID NO:2).

FIG. 4. Alignment of human DPP9 amino acid sequence beginning with residue 140 of SEQ ID NO: 2 (lower sequence) with the amino acid sequence encoded by a predicted open reading frame of GDD (SEQ ID NO: 9; upper sequence).

FIG. 5. Alignment of a predicted murine DPP9 (SEQ ID NO: 4; lower) from expressed sequence tags and human DPP9 amino acid sequences (SEQ ID NO: 2; upper).

FIG. 6. Alignment of murine (lower; SEQ ID NO: 3) and human DPP9 cDNA (upper; SEQ ID NO: 1) nucleotide sequences.

FIG. 8. Detection of murine DPP9 nucleotide sequence in two panels, where

DETAILED DESCRIPTION OF THE INVENTION

Examples

General

Figure 2:
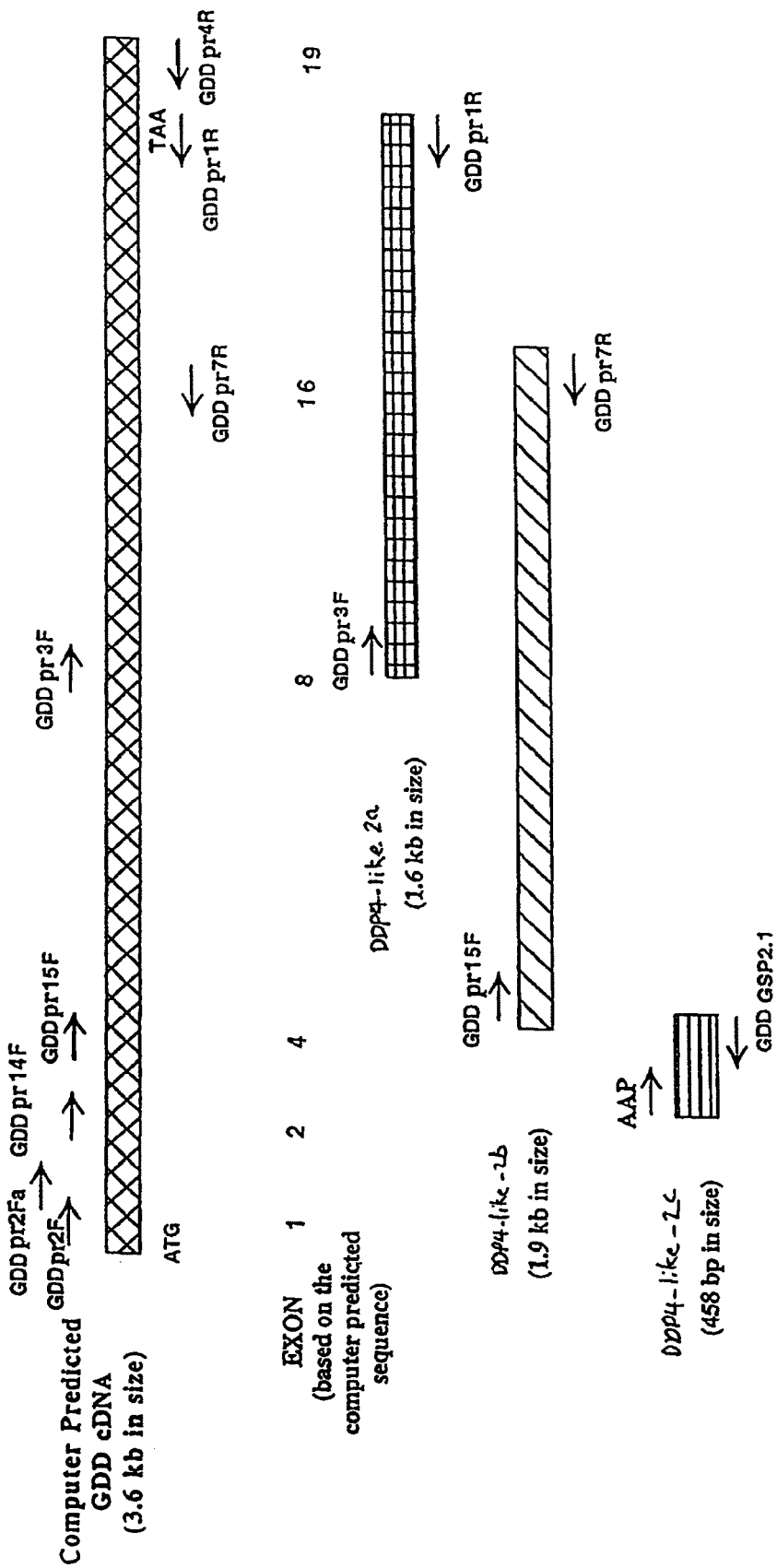
FIG. 2. Schematic representation of the cloning of human cDNA DPP9.
Figure 7:
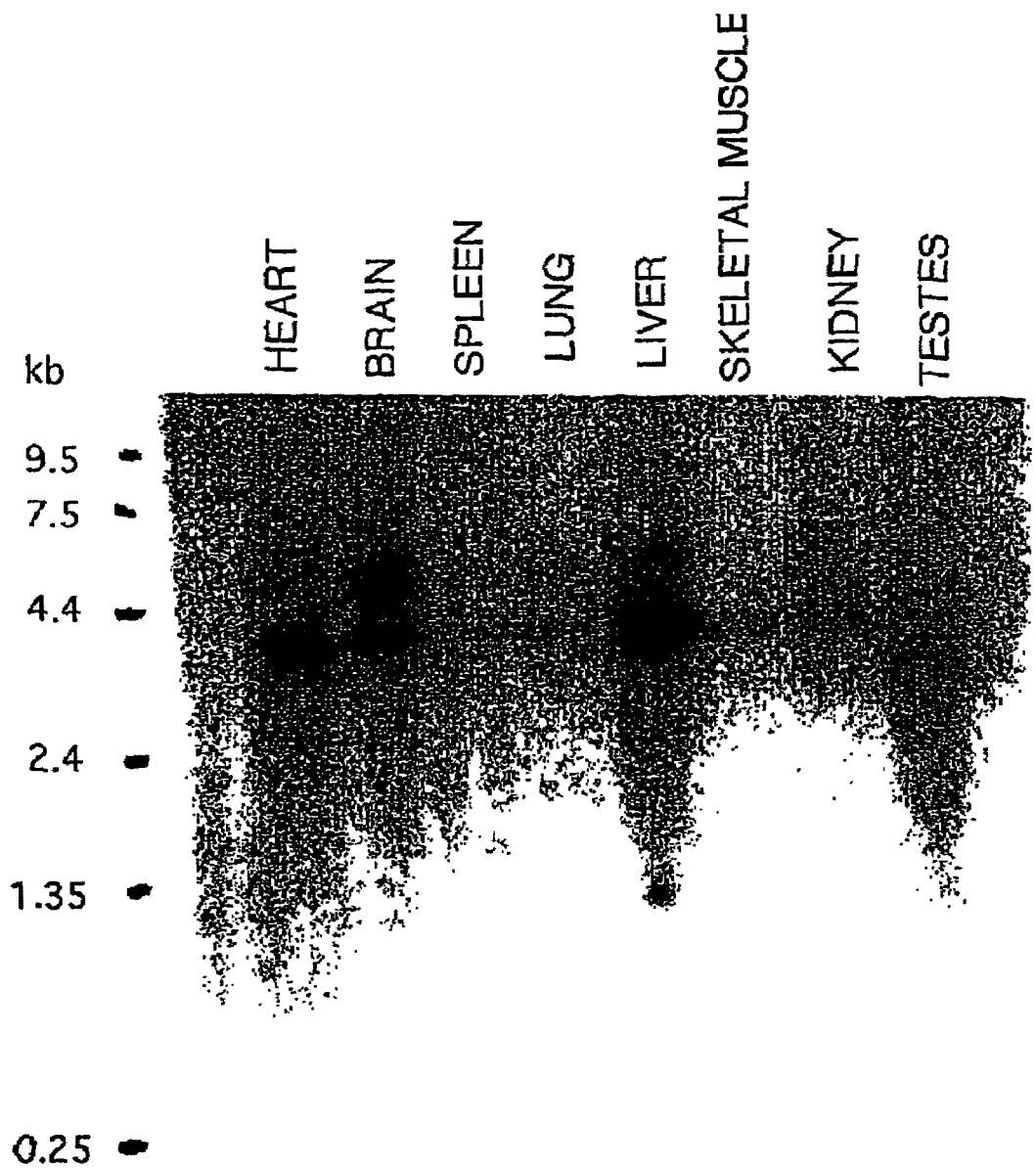
FIG. 7. Northern blot analysis of rat DPP9 RNA.

Restriction enzymes and other enzymes used in cloning were obtained from Boehringer Mannheim Roche. Standard molecular biology techniques were used unless indicated otherwise.

DPP9 Cloning

The nucleotide sequence of DPP8 shown in FIG. 1 was used to search the GenBank database for homologous nucleotide sequences. Nucleotide sequences referenced by GenBank accession numbers AC005594 and AC005783 were detected and named GDD. The GDD nucleotide sequence is 39.5 kb and has 19 predicted exons. The analysis of the predicted exon-intron boundaries in GDD suggests that the predicted open reading frame of GDD is 3.6 kb in length.

In view of the homology of DPP8 and the GDD nucleotide sequences, we hypothesised the existence of DPPIV-like molecules other than DPP8. We used oligonucleotide primers derived from the nucleotide sequence of GDD and reverse transcription PCR (RT-PCR) to isolate a cDNA encoding DPPIV-like molecules.

RT-PCR amplification of human liver RNA derived from a pool of 4 patients with autoimmune hepatitis using the primers GDD pr 1f and GDD pr 1r (Table 1) produced a 500 base pair product. This suggested that DPPIV-like molecules are likely to be expressed in liver cells derived from individuals with autoimmune hepatitis and that RNA derived from these cells is likely to be a suitable source for isolating cDNA clones encoding DPPIV-like molecules.

Primers GDD pr 3f and GDD pr 1r (Table 1) were then used to isolate a cDNA clone encoding a DPP4-like molecule. Primers GDD pr1f and GDD pr 7r (Table 1) were then used to isolate a cDNA clone encoding a DPP4-like molecule. A 1.9 kb product was observed and named DPP4-like-2b. As described further herein, the sequence of DPP4-like-2b overlaps with the sequence of DPP4-like-2a.

The DPP4-like-2a and 2b fragments were gel purified using WIZARD®PCR preps kit and cloned into the pGEM®-T-easy plasmid vector using the EcoRI restriction sites. The ligation reaction was used to transform JM 109 competent cells. The plasmid DNA was prepared by miniprep. The inserts were released by EcoRI restriction digestion. The DNA was sequenced in both directions using the M13Forward and M13Reverse sequencing primers. The complete sequence of DPP4-like-2a and 2b fragments was derived by primer walking.

The nucleotide sequence 5' adjacent to DPP4-like-2b was obtained by 5'RACE using dC tailing and the gene specific primers GDD GSP1.1 and 2.1 (Table 1). A fragment of 500 base pairs (DPP4-like-2c) was observed. The fragment was gel purified using WIZARD®PCR preps kit and cloned into the pGEM®-T-easy plasmid vector using the EcoRI restriction sites. The ligation reaction was used to transform JM109 competent cells. The plasmid DNA was prepared by miniprep. The inserts were released by EcoRI restriction digestion. The DNA was sequenced in both directions using the M13Forward and M13Reverse sequencing primers.

We identified further sequences, BE727051 and BE244612, with identity to the 5' end of DPP9. These were discovered while performing BLASTn with the 5' end of the DPP9 nucleotide sequence. BE727051 contained further 5' sequence for DPP9, which was also present in the genomic sequence for DPP9 on chromosome 19p13.3. This was used to design primer DPP9-22F (5'GCCGGCGGGTCCCCTGT-GTCCG3'), (SEQ ID NO: 34). Primer 22F was used in conjunction with primer GDD3' end (5'GGGCGGGACAAAGT-GCCTCACTGG3'), (SEQ ID NO:35) on cDNA made from the human CEM cell line to produce a 3000 bp product as expected.

Nucleotide Sequence Analysis of DPP4-like-2a, 2b, and 2c Fragments.

An analysis of the nucleotide sequence of fragments DPP4-like 2a, 2b and 2c with the Sequencher™ version 3.0 computer program, and the 5' fragment isolated by primers DPP9-22F and GDD3'end, revealed the nucleotide sequence shown in FIG. 3.

The predicted amino acid sequence shown in FIG. 3 was compared to a predicted amino acid sequence encoded by a predicted open reading frame of GDD (predicted from the nucleotide sequence referenced by GenBank Accession Nos. AC005594 and AC005783), to determine the relatedness of the nucleotide sequence of FIG. 3 to the nucleotide sequence of the predicted open reading frame of GDD (FIG. 4). Regions of amino acid identity were observed suggesting that there may be regions of nucleotide sequence identity of the predicted open reading frame of GDD and the sequence of FIG. 3. However, as noted in FIG. 4, there are regions of amino acid sequence encoded by the sequence of FIG. 3 and the amino acid sequence encoded by the predicted open reading frame of GDD which are not identical, demonstrating that the nucleotide sequences encoding the predicted open reading frame of GDD and the sequence shown in FIG. 3 are different nucleotide sequences.

As described further herein, the predicted amino acid sequence encoded by the cDNA sequence shown in FIG. 3 is homologous to the amino acid sequence of DPP8. Accordingly, and as a cDNA consisting of the nucleotide sequence shown in FIG. 3 was not known, the sequence shown in FIG. 3 was named cDNA DPP9.

The predicted amino acid sequence encoded by cDNA DPP9 (called DPP9) is 969 amino acids and is shown in FIG. 3. The alignment of DPP9 and DPP8 amino acid sequences suggests that the nucleotide sequence shown in FIG. 3 may be a partial length clone. Notwithstanding this point, as discussed below, the inventors have found that the alignment of DPP9 amino acid sequence with the amino acid sequences of DPP8, DPP4 and FAP shows that DPP9 comprises sequence necessary for providing enzymolysis and utility. In view of the similarity between DPP9 and DPP8, a full length clone may be of the order of 882 amino acids. A full length clone could be obtained by standard techniques, including for example, the RACE technique using an oligonucleotide primer derived from the 5' end of cDNA DPP9.

In view of the homology between the DPP8 and DPP9 amino acid sequences, it is likely that cDNA DPP9 encodes an amino acid sequence which has dipeptidyl peptidase enzymatic activity. Specifically, it is noted that the DPP9 amino acid sequence contains the catalytic triad Ser-Asp-His in the order of a non-classical serine protease as required for the charge relay system. The serine recognition site characteristic of DPP4 and DPP4-like family members, GYSWGG, (SEQ ID NO:36), surrounds the serine residue also suggesting that DPP9 cDNA will encode a DPP4-like enzyme activity.

Further, DPP9 amino acid sequence also contains the two glutamic acid residues located at positions 205 and 206 in DPPIV. These are believed to be essential for the dipeptidyl peptidase enzymatic activity. By sequence alignment with DPPIV, the residues in DPP8 predicted to play a pivotal role in the pore opening mechanism in Blade 2 of the propeller are $E^{259}$, $E^{260}$. These are equivalent to the residues $Glu^{205}$ and $Glu^{206}$ in DPPIV which previously have been shown to be essential for DPPIV enzyme activity. A point mutation $Glu^{259}Lys$ was made in DPP8 cDNA using the Quick Change Site directed Mutagenesis Kit (Stratagene, La Jolla). COS-7 cells transfected with wildtype DPP8 cDNA stained positive for H-Ala-Pro4 MbNA enzyme activity while the mutant cDNA gave no staining. Expression of DPP8 protein was demonstrated in COS cells transfected with wildtype and mutant cDNAs by immunostaining with anti-VS mAB. This mAB detects the V5 epitope that has been tagged to the C-terminus of DPP8 protein. Point mutations were made to each of the catalytic residues of DPP8, Ser739A, Asp817Ala and His849Ala, and each of these residues were also determined to be essential for DPP8 enzyme activity. In summary, the residues that have been shown experimentally to be required for enzyme activity in DPPIV and DPP8 are present in the DPP9 amino acid sequence: $Glu^{354}$, $Glu^{355}$, $Ser^{136}$, $Asp^{914}$ and $His^{946}$.

The DPP9 amino acid sequence shows the closest relatedness to DPP8, having 77% amino acid similarity and 60% amino acid identity. The relatedness to DPPIV is 25% amino acid identity and 47% amino acid similarity. The % similarity was determined by use of the program/algorithm "GAP" which is available from Genetics Computer Group (GCG), Wisconsin.

DPP9 mRNA Expression Studies

DPP4-like-2a was used to probe a Human Master RNA Blot™ (CLONTECH Laboratories Inc., USA) to study DPP9 tissue expression and the relative levels of DPP9 mRNA expression.

The DPP4-like-2a fragment hybridised to all tissue mRNA samples on the blot. The hybridisation also indicated high levels of DPP9 expression in most of the tissues samples on the blot (data not shown).

The DPP4-like-2a fragment was then used to probe two Multiple Tissue Northern Blots™. (CLONTECH Laboratories Inc., USA) to examine the mRNA expression and to determine the size of DPP9 mRNA transcript.

The autoradiographs of the DPP9 transcript was seen in all tissues examined confirming the results obtained from the Master RNA blot. A single major transcript 4.4 kb in size was seen in all tissues represented on two Blots after 16 hours of exposure. Weak bands could also be seen in some tissues after 6 hours of exposure. The DPP9 transcript was smaller than the 5.1 kb mRNA transcript of DPP8. A minor, very weak transcript 4.8 kb in size was also seen in the spleen, pancreas, peripheral blood leukocytes and heart. The highest mRNA expression was observed in the spleen and heart. Of all tissues examined the thymus had the least DPP9 mRNA expression. The Multiple Tissue Northern Blots were also probed with a β-actin positive control. A 2.0 kb band was seen in all tissues. In addition as expected a 1.8 kb β-actin band was seen in heart and skeletal muscle.

Rat DPP9 Expression

A Rat Multiple Tissue Northern Blot (CLONTECH Laboratories, Inc., USA; catalogue #: 7764-1) was hybridized with a human DPP9 radioactively labeled probe, made using Megaprime DNA Labeling kit and $^{32}$P dCTP (Amersham International plc, Amersham, UK). The DPP9 PCR product used to make the probe was generated using Met3F (GGCT-GAGAGGATGGCCACCACCGGG), (SEQ ID NO:37), as the forward primer and GDD3' end (GGGCGGGA-CAAAGTGCCTCCACTGG), (SEQ ID NO:35), as the reverse primer. The hybridization was carried out according to the manufacturers' instructions at 60° C. to detect cross-species hybridization. After overnight hybridization the blot was washed at room temperature (2×SSC, 0.1% SDS) then at 40° C. (0.1.times.SSC, 0.1% SDS).

The human cDNA probe identified two bands in all tissues examined except in testes. A major transcript of 4 kb in size was seen in all tissues except testes. This 4 kb transcript was strongly expressed in the liver, heart and brain. A second weaker transcript 5.5 kb in size was present in all tissues except skeletal muscle and testes. However in the brain the 5.5 kb transcript was expressed at a higher level than the 4.4 kb transcript. In the testes only one transcript approximately 3.5 kb in size was detected. Thus, rat DPP9 mRNA hybridised with a human DPP9 probe indicating significant homology between DPP9 of the two species. The larger 5.5 kb transcript observed may be due to crosshybridisation to rat DPP8.

Mouse DPP9 Expression

A Unigene cluster for Mouse DPP9 was identified (UniGene Cluster Mm.33185) by homology to human DPP9. An analysis of expressed sequence tags contained in this cluster and mouse genomic sequence (AC026385) for Chromosome 17 with the Sequencher™ version 3.0 computer program revealed the nucleotide sequence shown in FIG. 6. This 3517 bp cDNA encodes a 869 aa mouse DPP9 protein (missing N-terminus) with 91% amino acid identity and 94% amino acid similarity to human DPP9. The mouse DPP9 amino acid sequence also has the residues required for enzyme activity, Ser, Asp and His and the two Glu residues.

The primers mgdd-pr1F (5'ACCTGGGAGGAAGCAC-CCCACTGTG3'), (SEQ ID NO:38), and mgdd-pr4R (5'TTCCACCTGGTCCTCAATCTCC3'), SEQ ID NO:39), were designed from this sequence and used to amplify a 452 bp product as expected from liver mouse cDNA, as described below.

RNA Preparation

B57B16 mice underwent carbon tetrachloride treatment to induce liver fibrosis. Liver RNA were prepared from snap-frozen tissues using the TRIzol®. Reagent and other standard methods.

cDNA Synthesis 2.mu.g of liver RNA was reverse-transcribed using SuperScript II RNase H-Reverse Transcriptase (Gibco BRL).

PCR

PCR using mDPP9-1F (ACCTGGGAGGAAGCAC-CCCACTGTG), (SEQ ID NO:40), as the forward primer and mDPP9-2R (CTCTCCACATGCAGGGCTACAGAC), (SEQ ID NO:41), as the reverse primer was used to synthesize a 550 bas pair mouse DPP9 fragment. The PCR products were generated using AmpliTaq Gold® DNA Polymerase. The PCR was performed as follows: denaturation at 95° C. for 10 min, followed by 35 cycles of denaturation at 95° C. for 30 seconds, primer annealing at 60° C. for 30 seconds, and an extension 72° C. for 1 min.

Southern Blot

Figure 8A:
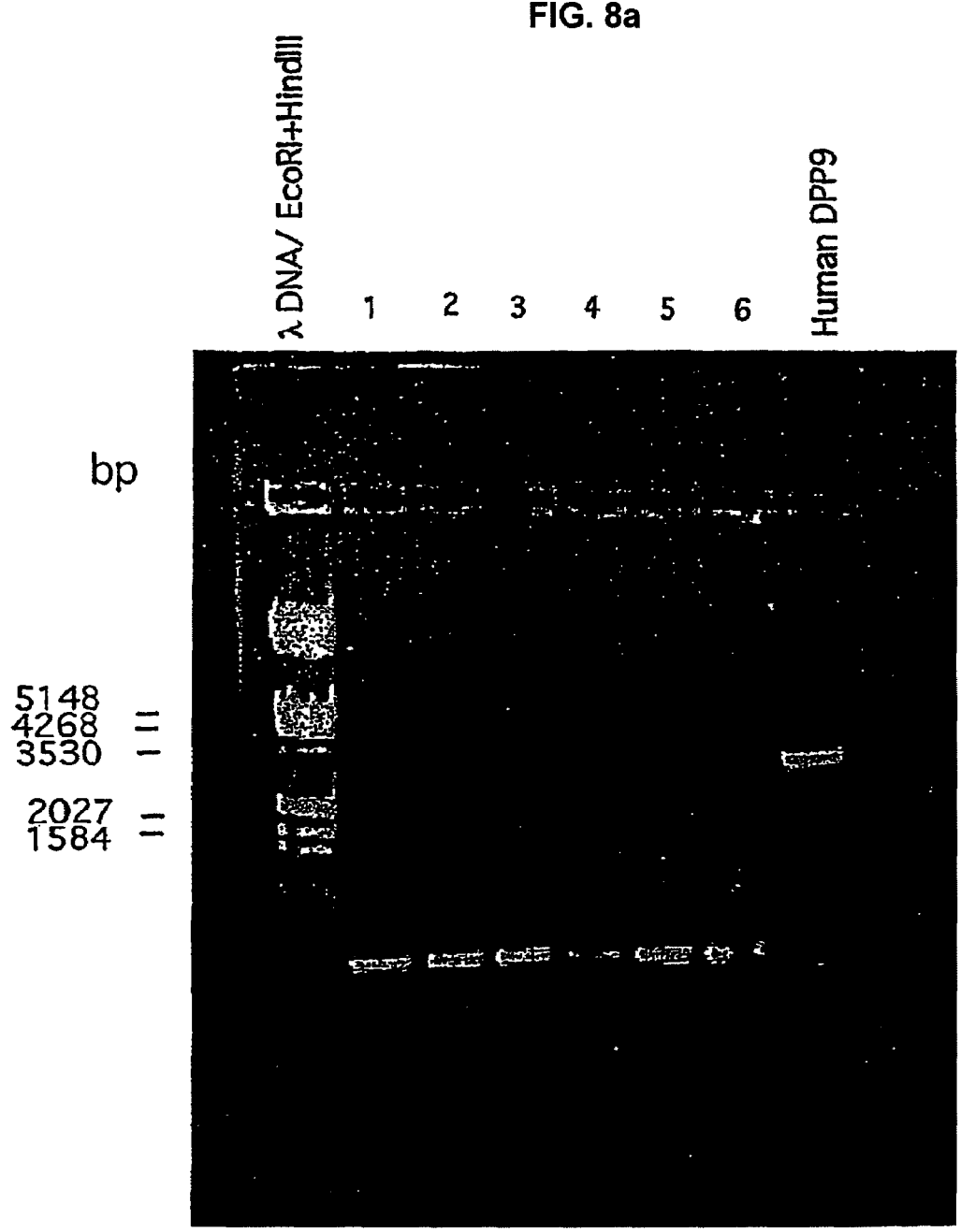
FIG. 8A is a gel showing DPP9 liver cDNA and FIG. 8B is a Southern blot of the gel of FIG. 8A.
Figure 8B:
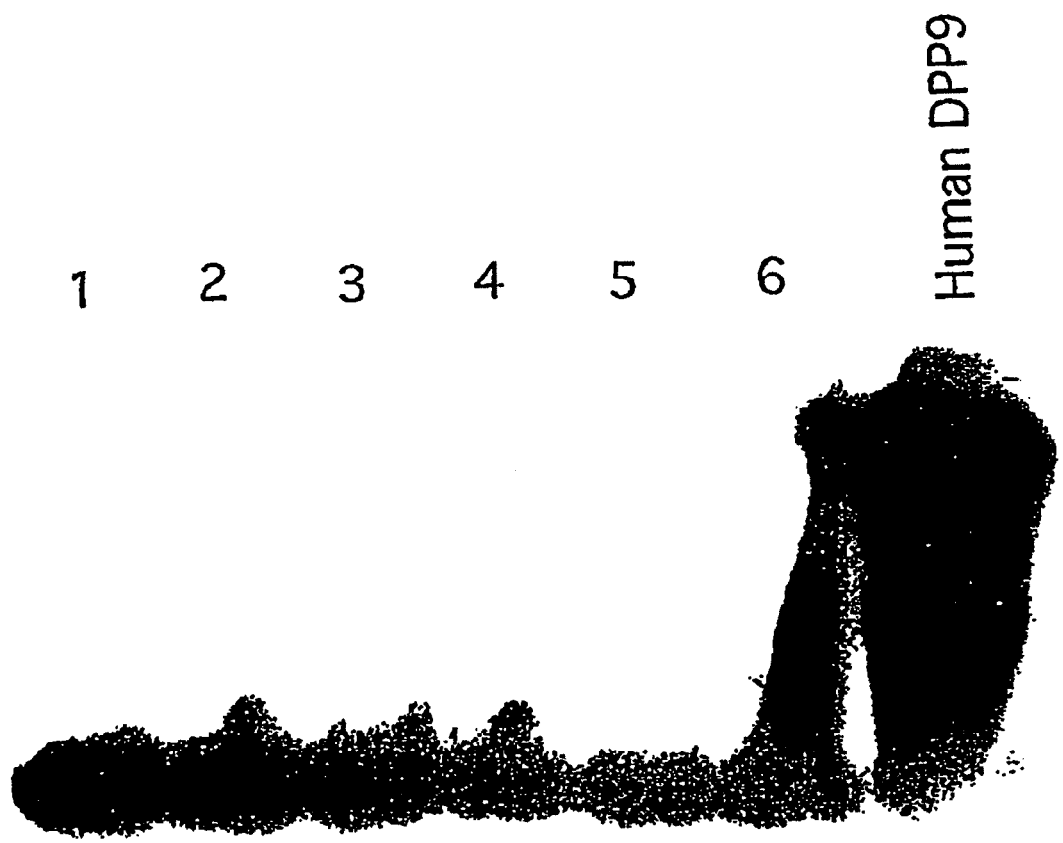

DPP9 PCR products from six mice as well as the largest human DPP9 PCR product were run on a 1% agarose gel. The DNA on the gel was then denatured using 0.4 M NaOH and transferred onto a Hybond-N+ membrane (Amersham International plc, Amersham, UK). The largest human DPP9 PCR product was radiolabeled using the Megaprime DNA Labeling kit and [$32^P$] dCTP (Amersham International plc, Amersham, UK). Unincorporated label was removed using a NAP column (Pharmacia Biotech, Sweden) and the denatured probe was incubated with the membrane for 2 hours at 60° C. in Express Hybridisation solution (CLONTECH Laboratories, Inc., USA). (FIG. 8). Thus, DPP9 mRNA of appropriate size was detected in fibrotic mouse liver using rt-PCR. Furthermore, the single band of mouse DPP9 cDNA hybridised with a human DPP9 probe indicating significant homology between DPP9 of the two species.

REFERENCES

1. Abbott C A, G W McCaughan & M D Gorrell 1999 Two highly conserved glutamic acid residues in the predicted beta propeller domain of dipeptidyl peptidase IV are required for its enzyme activity FEBS Letters 458: 278-84.

2. Abbott C A, D M T Yu, G W McCaughan & M D Gorrell 2000 Post proline peptidases having DP IV like enzyme activity Advances in Experimental Medicine and Biology 477: 103-9.

3. McCaughan G W, M D Gorrell, G A Bishop, C A Abbott, N A Shackel, P H McGuinness, M T Levy, A F Sharland, D G Bowen, D Yu, L Slaitini, W B Church & J Napoli 2000 Molecular pathogenesis of liver disease: an approach to hepatic inflammation, cirrhosis and liver transplant tolerance Immunological Reviews 174: 172-91.

4. Scanlan M J, B K Raj, B Calvo, P Garin-Chesa, M P Sanz-Moncasi, J H Healey, L J Old & W J Rettig 1994 Molecular cloning of fibroblast activation protein alpha, a member of the serine protease family selectively expressed in stromal fibroblasts of epithelial cancers Proceedings of the National Academy of Sciences United States of America 91: 5657-61.

5. Handbook of Proteolytic Enzymes. Barrett A J, N D Rawlings & J F Woess. 1998., London: Academic Press. 1666.

6. Jacotot E, C Callebaut, J Blanco, B Krust, K Neubert, A Barth & A G Hovanessian 1996 Dipeptidyl-peptidase IV-beta, a novel form of cell-surface-expressed protein with dipeptidyl-peptidase IV activity European Journal of Biochemistry 239: 248-58.

7. Rawlings N D & A J Barrett 1999 MEROPS: the peptidase database Nucleic Acids Research 27: 325-31.

8. Park J E, M C Lenter, R N Zimmermann, P Garin-Chesa, L J Old & W J Rettig 1999 Fibroblast activation protein: A dual-specificity serine protease expressed in reactive human tumor stromal fibroblasts Journal of Biological Chemistry 274: 36505-12.

9. Levy M T, G W McCaughan, C A Abbott, J E Park, A M Cunningham, E Muller, W J Rettig & M D Gorrell 1999 Fibroblast activation protein: A cell surface dipeptidyl peptidase and gelatinase expressed by stellate cells at the tissue remodelling interface in human cirrhosis Hepatology 29: 1768-78.

10. De Meester I, S Korom, J Van Damme & S Scharp 1999 CD26, let it cut or cut it down Immunology Today 20: 367-75.

11. Natural substrates of dipeptidyl peptidase IV. De Meester I, C Durinx, G Bal, P Proost, S Struyf, F Goossens, K Augustyns & S Scharp. 2000, in Cellular Peptidases in Immune Functions and Diseases II, J Langner & S Ansorge, Editor. Kluwer: New York. p. 67-88.

12. Mentlein R 1999 Dipeptidyl-peptidase IV (CD26): role in the inactivation of regulatory peptides Regulatory Peptides 85: 9-24.

13. Morrison M E, S Vijayasaradhi, D Engelstein, A P Albino & A N Houghton 1993 A marker for neoplastic progression of human melanocytes is a cell surface ectopeptidase Journal of Experimental Medicine 177: 1135-43.

14. Mueller S C, G Ghersi, S K Akiyama, Q X A Sang, L Howard, M Pineiro-Sanchez, H Nakahara, Y Yeh & W T Chen 1999 A novel protease-docking function of integrin at invadopodia Journal of Biological Chemistry 274: 24947-52.

15. Holst J J & C F Deacon 1998 Inhibition of the activity of dipeptidyl-peptidase IV as a treatment for type 2 diabetes Diabetes 47: 1663-70.

16. Marguet D, L Baggio, T Kobayashi, A M Bernard, M Pierres, P F Nielsen, U Ribel, T Watanabe, D J Drucker & N Wagtmann 2000 Enhanced insulin secretion and improved glucose tolerance in mice lacking CD26 Proceedings of the National Academy of Sciences of the United States of America 97: 6874-9.

17. Ohtsuki T, H Tsuda & C Morimoto 2000 Good or evil: CD26 and HIV infection Journal of Dermatological Science 22: 152-60.

18. Wesley U V, A P Albino, S Tiwari & A N Houghton 1999 A role for dipeptidyl peptidase IV in suppressing the malignant phenotype of melanocytic cells Journal of Experimental Medicine 190: 311-22.

19. Korom S, I De Meester, T H W Stadlbauer, A Chandraker, M Schaub, M H Sayegh, A Belyaev, A Haemers, S Scharp & J W Kupiecweglinski 1997 Inhibition of CD26/dipeptidyl peptidase IV activity in vivo prolongs cardiac allograft survival in rat recipients Transplantation 63: 1495-500.

20. Tanaka S, T Murakami, H Horikawa, M Sugiura, K Kawashima & T Sugita 1997 Suppression of arthritis by the inhibitors of dipeptidyl peptidase IV International Journal of Immunopharmacology 19: 15-24.

21. Augustyns K, G Bal, G Thonus, A Belyaev, X M Zhang, W Bollaert, A M Lambeir, C Durinx, F Goossens & A Haemers 1999 The unique properties of dipeptidyl-peptidase IV (DPP IV/CD26) and the therapeutic potential of DPP IV inhibitors Current Medicinal Chemistry 6: 311-27.

22. Hinke S A, J A Pospisilik, H U Demuth, S Mannhart, K Kuhn-Wache, T Hoffmannn, E Nishimura, R A Pederson & C H S McIntosh 2000 Dipeptidyl peptidase IV (DPIV/CD26) degradation of glucagon—Characterization of glucagon degradation products and DPIV-resistant analogs Journal of Biological Chemistry 275: 3827-34.

23. Korom S, I De Meester, A Coito, E Graser, H D Volk, K Schwemmle, S Scharpe & J W Kupiec-Weglinski 1999 Immunomodulatory influence of CD26 dipeptidylpeptidase IV during acute and accelerated rejection Langenbecks Archives of Surgery 1: 241-5.

24. Tavares W, D J Drucker & P L Brubaker 2000 Enzymatic- and renal-dependent catabolism of the intestinotropic hormone glucagon-like peptide-2 in rats American Journal of Physiology Endocrinology and Metabolism 278: E134-E9.

25. David F, A M Bernard, M Pierres & D Marguet 1993 Identification of serine 624, aspartic acid 702, and histidine 734 as the catalytic triad residues of mouse dipeptidyl-peptidase IV (CD26). A member of a novel family of nonclassical serine hydrolases J Biol Chem 268: 17247-52.

26. Ogata S, Y Misumi, E Tsuji, N Takami, K Oda & Y Ikehara 1992 Identification of the active site residues in dipeptidyl peptidase IV by affinity labeling and site-directed mutagenesis Biochemistry 31: 2582-7.

27. Dipeptidyl peptidase IV (DPPIV/CD26): biochemistry and control of cell-surface expression. Trugnan G, T Ait-Slimane, F David, L Baricault, T Berbar, C Lenoir & C Sapin. 1997, in Cell-Surface Peptidases in Health and Disease, A J Kenny & C M Boustead, Editor. BIOS Scientific Publishers: Oxford. p. 203-17.

28. Steeg C, U Hartwig & B Fleischer 1995 Unchanged signaling capacity of mutant CD26/dipeptidylpeptidase IV molecules devoid of enzymatic activity Cell Immunol 164: 311-5.

29. Fulop V, Z Bocskei & L Polgar 1998 Prolyl oligopeptidase—an unusual beta-propeller domain regulates proteolysis Cell 94: 161-70.

30. Ausubel F M, R Brent, R E Kingston, D D Moore, J G Seidman, J A Smith & K Struhl, ed. Current Protocols in Molecular Biology. 1998, John Wiley & Sons: USA.

31. Molecular cloning: a laboratory manual. Sambrook J, E F Fritsch & T Maniatis. 1989. 2nd ed., Cold Spring Harbor: Cold Spring Harbor Laboratory Press.

32. Augustyns K J L, A M Lambeir, M Borloo, I Demeester, I Vedernikova, G Vanhoof, D Hendriks, S Scharpe & A Haemers 1997 Pyrrolidides—synthesis and structure-activity relationship as inhibitors of dipeptidyl peptidase IV European Journal of Medicinal Chemistry 32: 301-9.

33. Stockel-Maschek A, C Mrestani-Klaus, B Stiebitz, H U Demuth & K Neubert 2000 Thioxo amino acid pyrrolidides and thiazolidides: new inhibitors of proline specific peptidases Biochimica et Biophysica Acta—Protein Structure & Molecular Enzymology 1479: 15-31.

34. Schon, I Born, H U Demuth, J Faust, K Neubert, T Steinmetzer, A Barth & S Ansorge 1991 Dipeptidyl peptidase IV in the immune system. Effects of specific enzyme inhibitors on activity of dipeptidyl peptidase IV and proliferation of human lymphocytes Biological Chemistry Hoppe Seyler 372: 305-11.

35. Coligan J E, A M Kruisbeek, D H Margulies, E M Shevach & W Strober, eds. Current Protocols in Immunology. 1998, John Wiley & Sons: USA.

36. Fibroblast activation protein. Rettig W J. 1998, in Handbook of Proteolytic Enzymes, A J Barrett, N D Rawlings & J F Woessner, Editor. Academic Press: San Diego. p. 387-9.

TABLE 1

|  | Primer length | Primer sequence (5'-3') |
|---|---|---|
| FORWARD primer name | | |
| GDD pr 1f | 24 mer | GTG GAG ATC GAG GAC CAG GTG GAG |
| GDD pr 2f | 24 mer | CAA AGT GAG GAA AAA TGC ACT CCG |
| GDD pr 2a | 24 mer | TGA GGA AAA ATG CAC TCC GAG CAG |
| GDD pr 3f | 24 mer | AAA CTG GCT GAG TTC CAG ACT GAC |
| GDD pr 5f | 24 mer | CGG GGA AGG TGA GCA GAG CCT GAC |
| GDD pr 6f | 24 mer | AGA AGC ACC CCA CCG TCC TCT TTG |
| GDD pr 11f | 24 mer | GAG AAG GAG CTG GTG CAG CCC TTC |
| GDD pr 12f | 24 mer | TCA GAG GGA GAG GAC GAG CTC TGC |
| GDD pr 14f | 24 mer | CCG CTT CCA GGT GCA GAA GCA CTC |
| GDD pr 15f | 24 mer | CTA CGA CTT CCA CAG CGA GAG TGG |
| GDD pr 16f | 25 mer | GAT GAG TCC GAG GTG GAG GTC ATT C |
| REVERSE Primer name | | |
| GDD pr 1r | 24 mer | GCT CAG AGG TAT TCC TGT AGA AAG |
| GDD pr 4r | 24 mer | CCC ATG TTG GCC AGG CTG GTC TTG |
| GDD pr 7r | 24 mer | AGG ACC AGC CAT GGA TGG CAA CTC |
| GDD pr 8r | 24 mer | CCG CTC AGC TTG TAG ACG TGC ACG |
| GDD pr 9r | 24 mer | TCA TTC TCT GTG CTC GGG ATG AAC |
| GDD pr 13r | 24 mer | GCA CAT CCG AGC GCG TGT GGA AAT |
| GDD pr 17r | 24 mer | TGG GAG AAG CCG GGC GTG GTG AGG |
| GDD pr 18r | 25 mer | GCG GTC GAA CTC TTC CTG TAT GAC G |
| 5'RACE Primer name | | |
| GDD GSP 1.1 | 18 mer | TGA AGG AGA AGA AGG CAG |
| GDD GSP 2.1 | 24 mer | CCT GAG CAC TGG GTC TTG ATT TCC |
| 5' RACE Abridged Anchor Primer (AAP) | 36 mer | GGC CAC GCG TCG ATC ATG ACG GGI IGG GII GGG IIG |

SEQUENCE LISTING

<160> NUMBER OF SEQ ID NOS: 57

<210> SEQ ID NO 1
<211> LENGTH: 3000
<212> TYPE: DNA
<213> ORGANISM: Homo sapiens

<400> SEQUENCE: 1

```
cggcgggtcc cctgtgtccg ccgcggctgt cgtcccccgc tcccgccact tccggggtcg      60
cagtcccggg catggagccg cgaccgtgag gcgccgctgg acccgggacg acctgcccag     120
tccggccgcc gccccacgtc ccggtctgtg tcccacgcct gcagctggaa tggaggctct     180
ctggaccctt tagaaggcac ccctgccctc ctgaggtcag ctgagcggtt aatgcggaag     240
gttaagaaac tgcgcctgga caaggagaac accggaagtt ggagaagctt ctcgctgaat     300
tccgaggggg ctgagaggat ggccaccacc gggacccaa cggccgaccg aggcgacgca      360
gccgccacag atgacccggc cgcccgcttc caggtgcaga agcactcgtg ggacgggctc     420
cggagcatca tccacggcag ccgcaagtac tcgggcctca ttgtcaacaa ggcgccccac     480
gacttccagt ttgtgcagaa gacggatgag tctgggcccc actccaccg cctctactac      540 ctgggaatgc catatggcag ccgggagaac tccctcctct actctgagat tcccaagaag     600
gtccggaaag aggctctgct gctcctgtcc tggaagcaga tgctggatca tttccaggcc     660
acgccccacc atgggtctca ctctcgggag gaggagctgc tgagggagcg gaaacgcctg     720
ggggtcttcg gcatcacctc ctacgacttc acacagcgaga gtggcctctt cctcttccag     780
gccagcaaca gcctcttcca ctgccgcgac ggcggcaaga acggcttcat ggtgtcccct     840
```

```
atgaaaccgc tggaaatcaa gacccagtgc tcagggcccc ggatggaccc caaaatctgc    900
cctgccgacc ctgccttctt ctccttcaac aataacagcg acctgtgggt ggccaacatc    960
gagacaggcg aggagcggcg gctgaccttc tgccaccaag gtttatccaa tgtcctggat   1020
gaccccaagt ctgcgggtgt ggccaccttc gtcatacagg aagagttcga ccgcttcact   1080
gggtactggt ggtgccccac agcctcctgg aaggttcag agggcctcaa gacgctgcga    1140
atcctgtatg aggaagtcga tgagtccgag gtggaggtca ttcacgtccc ctctcctgcg   1200
ctagaagaaa ggaagacgga ctcgtatcgg taccccagga caggcagcaa gaatcccaag   1260
attgccttga aactggctga gttccagact gacagccagg gcaagatcgt ctcgacccag   1320
gagaaggagc tggtgcagcc cttcagctcg ctgttcccga aggtggagta catcgccagg   1380
gccgggtgga cccgggatgg caaatacgcc tgggccatgt tcctggaccg gccccagcag   1440
tggctccagc tcgtcctcct cccccggcc ctgttcatcc cgagcacaga gaatgaggag    1500
cagcggctag cctctgccag agctgtcccc aggaatgtcc agccgtatgt ggtgtacgag   1560
gaggtcacca acgtctggat caatgttcat gacatcttct atcccttccc ccaatcagag   1620
ggagaggacg agctctgctt ctccgcgcc aatgaatgca agaccggctt ctgccatttg    1680
tacaaagtca ccgccgtttt aaaatcccag ggctacgatt ggagtgagcc cttcagcccc   1740
ggggaagatg aatttaagtg ccccattaag gaagagattc tctgaccag cggtgaatgg    1800
gaggttttgg cgaggcacgg ctccaagatc tgggtcaatg aggagaccaa gctggtgtac   1860
ttccagggca ccaaggacac gccgctggag caccacctct acgtggtcag ctatgaggcg   1920
gccggcgaga tcgtacgcct caccacgccc ggcttctccc atagctgctc catgagccag   1980
aacttcgaca tgttcgtcag ccactacagc agcgtgagca cgccgccctg cgtgcacgtc   2040
tacaagctga gcggccccga cgacgacccc ctgcacaagc agccccgctt ctgggctagc   2100
atgatggagg cagccagctg ccccccggat tatgttcctc cagagatctt ccatttccac   2160
acgcgctcgg atgtgcggct ctacggcatg atctacaagc cccacgcctt gcagccaggg   2220
aagaagcacc ccaccgtcct ctttgtatat ggaggccccc aggtgcagct ggtgaataac   2280
tccttcaaag gcatcaagta cttgcggctc aacacactgg cctccctggg ctacgccgtg   2340
gttgtgattg acggcagggg ctcctgtcag cgagggcttc ggttcgaagg ggccctgaaa   2400
aaccaaatgg gccaggtgga gatcgaggac caggtggagg cctgcagtt cgtggccgag    2460
aagtatggct tcatcgacct gagccgagtt gccatccatg ctggtcta cgggggcttc     2520
ctctcgctca tgggctaat ccacaagccc caggtgttca aggtggccat cgcgggtgcc    2580
ccggtcaccg tctggatggc ctacgacaca gggtacactg agcgctacat ggacgtccct   2640
gagaacaacc agcacggcta tgaggcgggt tccgtgccc tgcacgtgga aagctgccc    2700
aatgagccca accgcttgct tatcctccac ggcttcctgg acgaaaacgt gcactttttc   2760
cacacaaact tcctcgtctc ccaactgatc cgagcaggga aaccttacca gctccagatc   2820
taccccaacg agagacacag tattcgctgc ccgagtcgg gcgagcacta tgaagtcacg    2880
ttactgcact ttctacagga ataccttga gcctgcccac cggagccgc cacatcacag     2940
cacaagtggc tgcagcctcc gcggggaacc aggcgggagg gactgagtgg cccgcgggcc   3000
```

<210> SEQ ID NO 2
<211> LENGTH: 969
<212> TYPE: PRT
<213> ORGANISM: Homo sapiens

<400> SEQUENCE: 2

```
Arg Arg Val Pro Cys Val Arg Arg Gly Cys Arg Pro Pro Leu Pro Pro
 1               5                  10                  15

Leu Pro Gly Ser Gln Ser Arg Ala Trp Ser Arg Asp Arg Glu Ala Pro
             20                  25                  30

Leu Asp Pro Gly Arg Pro Ala Gln Ser Gly Arg Arg Pro Thr Ser Arg
             35                  40                  45

Ser Val Ser His Ala Cys Ser Trp Asn Gly Gly Ser Leu Asp Pro Leu
 50                  55                  60

Glu Gly Thr Pro Ala Leu Leu Arg Ser Ala Glu Arg Leu Met Arg Lys
 65              70                  75                  80

Val Lys Lys Leu Arg Leu Asp Lys Glu Asn Thr Gly Ser Trp Arg Ser
                 85                  90                  95

Phe Ser Leu Asn Ser Glu Gly Ala Glu Arg Met Ala Thr Thr Gly Thr
                 100                 105                 110

Pro Thr Ala Asp Arg Gly Asp Ala Ala Thr Asp Asp Pro Ala Ala
             115                 120                 125

Arg Phe Gln Val Gln Lys His Ser Trp Asp Gly Leu Arg Ser Ile Ile
 130                 135                 140

His Gly Ser Arg Lys Tyr Ser Gly Leu Ile Val Asn Lys Ala Pro His
 145                 150                 155                 160

Asp Phe Gln Phe Val Gln Lys Thr Asp Glu Ser Gly Pro His Ser His
                 165                 170                 175

Arg Leu Tyr Tyr Leu Gly Met Pro Tyr Gly Ser Arg Glu Asn Ser Leu
             180                 185                 190

Leu Tyr Ser Glu Ile Pro Lys Lys Val Arg Lys Glu Ala Leu Leu Leu
             195                 200                 205

Leu Ser Trp Lys Gln Met Leu Asp His Phe Gln Ala Thr Pro His His
             210                 215                 220

Gly Val Tyr Ser Arg Glu Glu Leu Leu Arg Glu Arg Lys Arg Leu
 225                 230                 235                 240

Gly Val Phe Gly Ile Thr Ser Tyr Asp Phe His Ser Glu Ser Gly Leu
             245                 250                 255

Phe Leu Phe Gln Ala Ser Asn Ser Leu Phe His Cys Arg Asp Gly Gly
             260                 265                 270

Lys Asn Gly Phe Met Val Ser Pro Met Lys Pro Leu Glu Ile Lys Thr
             275                 280                 285

Gln Cys Ser Gly Pro Arg Met Asp Pro Lys Ile Cys Pro Ala Asp Pro
 290                 295                 300

Ala Phe Phe Ser Phe Asn Asn Asn Ser Asp Leu Trp Val Ala Asn Ile
 305                 310                 315                 320

Glu Thr Gly Glu Glu Arg Arg Leu Thr Phe Cys His Gln Gly Leu Ser
             325                 330                 335

Asn Val Leu Asp Asp Pro Lys Ser Ala Gly Val Ala Thr Phe Val Ile
             340                 345                 350

Gln Glu Glu Phe Asp Arg Phe Thr Gly Tyr Trp Trp Cys Pro Thr Ala
             355                 360                 365

Ser Trp Glu Gly Ser Glu Gly Leu Lys Thr Leu Arg Ile Leu Tyr Glu
 370                 375                 380

Glu Val Asp Glu Ser Glu Val Glu Val Ile His Val Pro Ser Pro Ala
 385                 390                 395                 400

Leu Glu Glu Arg Lys Thr Asp Ser Tyr Arg Tyr Pro Arg Thr Gly Ser
                 405                 410                 415
```

```
Lys Asn Pro Lys Ile Ala Leu Lys Leu Ala Glu Phe Gln Thr Asp Ser
            420                 425                 430

Gln Gly Lys Ile Val Ser Thr Gln Glu Lys Glu Leu Val Gln Pro Phe
        435                 440                 445

Ser Ser Leu Phe Pro Lys Val Glu Tyr Ile Ala Arg Ala Gly Trp Thr
450                 455                 460

Arg Asp Gly Lys Tyr Ala Trp Ala Met Phe Leu Asp Arg Pro Gln Gln
465                 470                 475                 480

Trp Leu Gln Leu Val Leu Pro Ala Leu Phe Ile Pro Ser Thr
                485                 490                 495

Glu Asn Glu Glu Gln Arg Leu Ala Ser Ala Arg Ala Val Pro Arg Asn
                500                 505                 510

Val Gln Pro Tyr Val Val Tyr Glu Glu Val Thr Asn Val Trp Ile Asn
            515                 520                 525

Val His Asp Ile Phe Tyr Pro Phe Pro Gln Ser Glu Gly Glu Asp Glu
        530                 535                 540

Leu Cys Phe Leu Arg Ala Asn Glu Cys Lys Thr Gly Phe Cys His Leu
545                 550                 555                 560

Tyr Lys Val Thr Ala Val Leu Lys Ser Gln Gly Tyr Asp Trp Ser Glu
                565                 570                 575

Pro Phe Ser Pro Gly Glu Asp Glu Phe Lys Cys Pro Ile Lys Glu Glu
            580                 585                 590

Ile Ala Leu Thr Ser Gly Glu Trp Glu Val Leu Ala Arg His Gly Ser
            595                 600                 605

Lys Ile Trp Val Asn Glu Glu Thr Lys Leu Val Tyr Phe Gln Gly Thr
        610                 615                 620

Lys Asp Thr Pro Leu Glu His His Leu Tyr Val Val Ser Tyr Glu Ala
625                 630                 635                 640

Ala Gly Glu Ile Val Arg Leu Thr Thr Pro Gly Phe Ser His Ser Cys
                645                 650                 655

Ser Met Ser Gln Asn Phe Asp Met Phe Val Ser His Tyr Ser Ser Val
            660                 665                 670

Ser Thr Pro Pro Cys Val His Val Tyr Lys Leu Ser Gly Pro Asp Asp
        675                 680                 685

Asp Pro Leu His Lys Gln Pro Arg Phe Trp Ala Ser Met Met Glu Ala
        690                 695                 700

Ala Ser Cys Pro Pro Asp Tyr Val Pro Pro Glu Ile Phe His Phe His
705                 710                 715                 720

Thr Arg Ser Asp Val Arg Leu Tyr Gly Met Ile Tyr Lys Pro His Ala
                725                 730                 735

Leu Gln Pro Gly Lys Lys His Pro Thr Val Leu Phe Val Tyr Gly Gly
            740                 745                 750

Pro Gln Val Gln Leu Val Asn Asn Ser Phe Lys Gly Ile Lys Tyr Leu
            755                 760                 765

Arg Leu Asn Thr Leu Ala Ser Leu Gly Tyr Ala Val Val Ile Asp
770                 775                 780

Gly Arg Gly Ser Cys Gln Arg Gly Leu Arg Phe Glu Gly Ala Leu Lys
785                 790                 795                 800

Asn Gln Met Gly Gln Val Glu Ile Glu Asp Gln Val Glu Gly Leu Gln
                805                 810                 815

Phe Val Ala Glu Lys Tyr Gly Phe Ile Asp Leu Ser Arg Val Ala Ile
            820                 825                 830

His Gly Trp Ser Tyr Gly Gly Phe Leu Ser Leu Met Gly Leu Ile His
```

```
                     835                 840                 845
Lys Pro Gln Val Phe Lys Val Ala Ile Ala Gly Ala Pro Val Thr Val
    850                 855                 860

Trp Met Ala Tyr Asp Thr Gly Tyr Thr Glu Arg Tyr Met Asp Val Pro
865                 870                 875                 880

Glu Asn Asn Gln His Gly Tyr Glu Ala Gly Ser Val Ala Leu His Val
                885                 890                 895

Glu Lys Leu Pro Asn Glu Pro Asn Arg Leu Leu Ile Leu His Gly Phe
                900                 905                 910

Leu Asp Glu Asn Val His Phe Phe His Thr Asn Phe Leu Val Ser Gln
            915                 920                 925

Leu Ile Arg Ala Gly Lys Pro Tyr Gln Leu Gln Ile Tyr Pro Asn Glu
            930                 935                 940

Arg His Ser Ile Arg Cys Pro Glu Ser Gly Glu His Tyr Glu Val Thr
945                 950                 955                 960

Leu Leu His Phe Leu Gln Glu Tyr Leu
                965
```

<210> SEQ ID NO 3
<211> LENGTH: 3287
<212> TYPE: DNA
<213> ORGANISM: Mus musculus

<400> SEQUENCE: 3

```
ccatcacagg agccccagag gatgtgcagc ggggtctccc cagttgagca ggtggccgca    60
ggggacatgg atgacacggc agcacgcttc tgtgtgcaga agcactcgtg ggatgggctg   120
cgtagcatta tccacggcag tcgcaagtcc tcgggcctca ttgtcagcaa ggccccccac   180
gacttccagt ttgtgcagaa gcctgacgag tctggccccc actctcaccg tctctattac   240
ctcggaatgc cttacggcag ccgtgagaac tccctcctct actccgagat ccccaagaaa   300
gtgcggaagg aggccctgct gctgctgtcc tggaagcaga tgctggacca cttccaggcc   360
acaccccacc atggtgtcta ctcccgagag gaggagctac tgcgggagcg caagcgcctg   420
ggcgtcttcg gaatcacctc ttatgacttc acagtgagag gcggcctctt cctcttccag   480
gccagcaata gcctgttcca ctgcagggat ggtggcaaga atggctttat ggtgtccccg   540
atgaagccac tggagatcaa gactcagtgt tctgggccac gcatggaccc caaaatctgc   600
cccgcagacc ctgccttctt ttccttcatc aacaacagtg atctgtgggt ggcaaacatc   660
gagactgggg aggaacggcg gctcaccttc tgtcaccagg gttcagctgg tgtcctggac   720
aatcccaaat cagcaggcgt ggccaccttt gtcatccagg aggagttcga ccgcttcact   780
gggtgctggt ggtgccccac ggcctcttgg aaggctccg aagtctcaa gacgctgcgc    840
atcctatatg aggaagtgga cgagtctgaa gtggaggtca ttcatgtgcc ctccccgcc    900
ctggaggaga ggaagacgga ctcctaccgc taccccagga caggcagcaa gaaccccaag   960
attgccctga gctggctga gctccagacg gaccatcagg gcaaaatcgt gtcaagctgc  1020
gagaaggaac tggtacagcc attcagctcc ctttttcccca aagtggagta catcgcccgg  1080
gctggctgga cacgggacgg caaatatgcc tgggccatgt tcctggaccg tccccagcaa  1140
cggcttcagc ttgtcctcct gcccctgct ctcttcatcc cggccgttga gagtgaggcc   1200
cagcggcagg cagctgccag agccgtcccc aagaatgtgc agccctttgt catctatgaa  1260
gaagtcacca atgtctggat caacgtccac gacatcttcc acccgtttcc tcaggctgag  1320
ggccagcagg actttgtttt ccttcgtgcc aacgaatgca agactggctt ctgccacctg  1380
```

-continued

| | |
|---|---|
| tacagggtca cagtggaact taaaaccaag gactatgact ggacggaacc cctcagccct | 1440 |
| acagaaggtg agtttaagtg ccccatcaag gaggaggtcg ccctgaccag tggcgagtgg | 1500 |
| gaggtcttgt cgaggcatgg ctccaagatc tgggtcaacg agcagacgaa gctggtgtac | 1560 |
| tttcaaggta caaaggacac accgctggaa catcacctct atgtggtcag ctacgagtca | 1620 |
| gcaggcgaga tcgtgcggct caccacgctc ggcttctccc acagctgctc catgagccag | 1680 |
| agcttcgaca tgttcgtgag tcactacagc agtgtgagca cgccaccctg tgtacatgtg | 1740 |
| tacaagctga gcggccccga tgatgaccca ctgcacaagc aaccacgctt ctgggccagc | 1800 |
| atgatggagg cagccaattg ccccccagac tatgtgcccc ctgagatctt ccacttccac | 1860 |
| acccgtgcag acgtgcagct ctacggcatg atctacaagc acacaccct gcaacctggg | 1920 |
| aggaagcacc ccactgtgct ctttgtctat gggggcccac aggtgcagtt ggtgaacaac | 1980 |
| tcctttaagg gcatcaaata cctgcggcta aatacactgg catccttggg ctatgctgtg | 2040 |
| gtggtgatcg atggtcgggg ctcctgtcag cggggcctgc acttcgaggg ggccctgaaa | 2100 |
| aatcaaatgg ccaggtggag gattgaggac caggtggaag gcttgcagta cgtggctgag | 2160 |
| aagtatggct tcattgactt gagccgagtc gccatccatg gctggtccta cggcggcttc | 2220 |
| ctctcactca tggggctcat ccacaagcca caagtgttca aggtagccat tgcgggcgct | 2280 |
| cctgtcactg tgtggatggc ctatgacaca gggtacacgg aacgatacat ggatgtcccc | 2340 |
| gaaaataacc agcaaggcta tgaggcaggg tctgtagccc tgcatgtgga aagctgccc | 2400 |
| aatgagccta accgctgct tatcctccac ggcttcctgg acgagaacgt tcacttcttc | 2460 |
| cacacaaatt tcctggtgtc ccagctgatc cgagcaggaa agccatacca gcttcagatc | 2520 |
| tacccaaacg agagacatag catccgctgc cgcgagtccg gagagcatta cgaggtgacg | 2580 |
| ctgctgcact ttctgcagga acacctgtga cctcagtccc gactcctgac gccaccgctg | 2640 |
| ctcttcttgc gtttttgtaa tcttttcatt tttgaagctt ccaatttgct tgctgctgct | 2700 |
| gctgcctggg ggccaggaca gaggtagtgg cggcccccat gccgccctcc ttgagctggt | 2760 |
| gaggagaagt cgccattgag cacacaacct ccaccagact gccatggccc cgaacctgca | 2820 |
| attccatcct agcgcagaag catgtgcctg ccacctgctg cccctgcaga gtcatgtgtg | 2880 |
| tttgtggtgg cattttaaa taattattta aagacagga agtaagcggt accgagcaat | 2940 |
| gaaactgaag gtacagcact gggcgtctgg ggaccccacg ctctcccaac gcccagacta | 3000 |
| tgtggagctg ccaagcccct gtctgggcac ctctgccctg cctgtctgct gcccggatcc | 3060 |
| tcctcactta gcacctaggg gtgtcagggt cgggagtagg acctgtcctg acctcagggt | 3120 |
| tatatatagc ccttccccac tccctcctac gagagttctg gcataaagaa gtaaaaaaaa | 3180 |
| aaaaaaaaaa aacaaacaaa aaaaccaaac cacctctaca tattatggaa agaaaatatt | 3240 |
| tttgtcaatt cttattcttt tataattatg tggtatgtag actcatt | 3287 |

<210> SEQ ID NO 4
<211> LENGTH: 869
<212> TYPE: PRT
<213> ORGANISM: Mus musculus protein

<400> SEQUENCE: 4

Pro Ser Gln Glu Pro Gln Arg Met Cys Ser Gly Val Ser Pro Val Glu
1               5                   10                  15

Gln Val Ala Ala Gly Asp Met Asp Asp Thr Ala Ala Arg Phe Cys Val
            20                  25                  30

```
Gln Lys His Ser Trp Asp Gly Leu Arg Ser Ile Ile His Gly Ser Arg
             35                  40                  45

Lys Ser Ser Gly Leu Ile Val Ser Lys Ala Pro His Asp Phe Gln Phe
 50                  55                  60

Val Gln Lys Pro Asp Glu Ser Gly Pro His Ser His Arg Leu Tyr Tyr
 65                  70                  75                  80

Leu Gly Met Pro Tyr Gly Ser Arg Glu Asn Ser Leu Leu Tyr Ser Glu
                     85                  90                  95

Ile Pro Lys Lys Val Arg Lys Glu Ala Leu Leu Leu Ser Trp Lys
                100                 105                 110

Gln Met Leu Asp His Phe Gln Ala Thr Pro His His Gly Val Tyr Ser
             115                 120                 125

Arg Glu Glu Leu Leu Arg Glu Arg Lys Arg Leu Gly Val Phe Gly
            130                 135                 140

Ile Thr Ser Tyr Asp Phe His Ser Glu Ser Gly Leu Phe Leu Phe Gln
145                 150                 155                 160

Ala Ser Asn Ser Leu Phe His Cys Arg Asp Gly Gly Lys Asn Gly Phe
                165                 170                 175

Met Val Ser Pro Met Lys Pro Leu Glu Ile Lys Thr Gln Cys Ser Gly
            180                 185                 190

Pro Arg Met Asp Pro Lys Ile Cys Pro Ala Asp Pro Ala Phe Phe Ser
            195                 200                 205

Phe Ile Asn Asn Ser Asp Leu Trp Val Ala Asn Ile Glu Thr Gly Glu
            210                 215                 220

Glu Arg Arg Leu Thr Phe Cys His Gln Gly Ser Ala Gly Val Leu Asp
225                 230                 235                 240

Asn Pro Lys Ser Ala Gly Val Ala Thr Phe Val Ile Gln Glu Glu Phe
                245                 250                 255

Asp Arg Phe Thr Gly Cys Trp Trp Cys Pro Thr Ala Ser Trp Glu Gly
            260                 265                 270

Ser Glu Gly Leu Lys Thr Leu Arg Ile Leu Tyr Glu Glu Val Asp Glu
            275                 280                 285

Ser Glu Val Glu Val Ile His Val Pro Ser Pro Ala Leu Glu Glu Arg
            290                 295                 300

Lys Thr Asp Ser Tyr Arg Tyr Pro Arg Thr Gly Ser Lys Asn Pro Lys
305                 310                 315                 320

Ile Ala Leu Lys Leu Ala Glu Leu Gln Thr Asp His Gln Gly Lys Ile
                325                 330                 335

Val Ser Ser Cys Glu Lys Glu Leu Val Gln Pro Phe Ser Ser Leu Phe
            340                 345                 350

Pro Lys Val Glu Tyr Ile Ala Arg Ala Gly Trp Thr Arg Asp Gly Lys
            355                 360                 365

Tyr Ala Trp Ala Met Phe Leu Asp Arg Pro Gln Gln Arg Leu Gln Leu
370                 375                 380

Val Leu Leu Pro Pro Ala Leu Phe Ile Pro Ala Val Glu Ser Glu Ala
385                 390                 395                 400

Gln Arg Gln Ala Ala Arg Ala Val Pro Lys Asn Val Gln Pro Phe
            405                 410                 415

Val Ile Tyr Glu Glu Val Thr Asn Val Trp Ile Asn Val His Asp Ile
                420                 425                 430

Phe His Pro Phe Pro Gln Ala Glu Gly Gln Gln Asp Phe Cys Phe Leu
            435                 440                 445

Arg Ala Asn Glu Cys Lys Thr Gly Phe Cys His Leu Tyr Arg Val Thr
```

-continued

```
        450                 455                 460
Val Glu Leu Lys Thr Lys Asp Tyr Asp Trp Thr Glu Pro Leu Ser Pro
465                 470                 475                 480

Thr Glu Gly Glu Phe Lys Cys Pro Ile Lys Glu Glu Val Ala Leu Thr
                485                 490                 495

Ser Gly Glu Trp Glu Val Leu Ser Arg His Gly Ser Lys Ile Trp Val
            500                 505                 510

Asn Glu Gln Thr Lys Leu Val Tyr Phe Gln Gly Thr Lys Asp Thr Pro
            515                 520                 525

Leu Glu His His Leu Tyr Val Val Ser Tyr Glu Ser Ala Gly Glu Ile
        530                 535                 540

Val Arg Leu Thr Thr Leu Gly Phe Ser His Ser Cys Ser Met Ser Gln
545                 550                 555                 560

Ser Phe Asp Met Phe Val Ser His Tyr Ser Ser Val Ser Thr Pro Pro
                565                 570                 575

Cys Val His Val Tyr Lys Leu Ser Gly Pro Asp Asp Pro Leu His
            580                 585                 590

Lys Gln Pro Arg Phe Trp Ala Ser Met Met Glu Ala Ala Asn Cys Pro
        595                 600                 605

Pro Asp Tyr Val Pro Pro Glu Ile Phe His Phe His Thr Arg Ala Asp
        610                 615                 620

Val Gln Leu Tyr Gly Met Ile Tyr Lys Pro His Thr Leu Gln Pro Gly
625                 630                 635                 640

Arg Lys His Pro Thr Val Leu Phe Val Tyr Gly Gly Pro Gln Val Gln
                645                 650                 655

Leu Val Asn Asn Ser Phe Lys Gly Ile Lys Tyr Leu Arg Leu Asn Thr
            660                 665                 670

Leu Ala Ser Leu Gly Tyr Ala Val Val Ile Asp Gly Arg Gly Ser
        675                 680                 685

Cys Gln Arg Gly Leu His Phe Glu Gly Ala Leu Lys Asn Gln Met Gly
        690                 695                 700

Gln Val Glu Ile Glu Asp Gln Val Glu Gly Leu Gln Tyr Val Ala Glu
705                 710                 715                 720

Lys Tyr Gly Phe Ile Asp Leu Ser Arg Val Ala Ile His Gly Trp Ser
                725                 730                 735

Tyr Gly Gly Phe Leu Ser Leu Met Gly Leu Ile His Lys Pro Gln Val
            740                 745                 750

Phe Lys Val Ala Ile Ala Gly Ala Pro Val Thr Val Trp Met Ala Tyr
        755                 760                 765

Asp Thr Gly Tyr Thr Glu Arg Tyr Met Asp Val Pro Glu Asn Asn Gln
        770                 775                 780

Gln Gly Tyr Glu Ala Gly Ser Val Ala Leu His Val Glu Lys Leu Pro
785                 790                 795                 800

Asn Glu Pro Asn Arg Leu Leu Ile Leu His Gly Phe Leu Asp Glu Asn
                805                 810                 815

Val His Phe Phe His Thr Asn Phe Leu Val Ser Gln Leu Ile Arg Ala
            820                 825                 830

Gly Lys Pro Tyr Gln Leu Gln Ile Tyr Pro Asn Glu Arg His Ser Ile
        835                 840                 845

Arg Cys Arg Glu Ser Gly Glu His Tyr Glu Val Thr Leu Leu His Phe
        850                 855                 860

Leu Gln Glu His Leu
865
```

<210> SEQ ID NO 5
<211> LENGTH: 3120
<212> TYPE: DNA
<213> ORGANISM: Homo sapiens

<400> SEQUENCE: 5

```
aagtgctaaa gcctccgagg ccaaggccgc tgctactgcc gccgctgctt cttagtgccg      60
cgttcgccgc ctgggttgtc accggcgccg ccgccgagga agccactgca accaggaccg     120
gagtggaggc ggcgcagcat gaagcggcgc aggcccgctc catagcgcac gtcgggacgg     180
tccgggcggg gccgggggga aggaaaatgc aacatggcag cagcaatgga aacagaacag     240
ctgggtgttg agatatttga aactgcggac tgtgaggaga atattgaatc acaggatcgg     300
cctaaattgg agccttttta tgttgagcgg tattcctgga gtcagcttaa aaagctgctt     360
gccgatacca gaaaatatca tggctacatg atggctaagg caccacatga tttcatgttt     420
gtgaagagga atgatccaga tggacctcat tcagacagaa tctattacct tgccatgtct     480
ggtgagaaca gagaaaatac actgttttat tctgaaattc ccaaaactat caatagagca     540
gcagtcttaa tgctctcttg gaagcctctt ttggatcttt tcaggcaac actggactat     600
ggaatgtatt ctcgagaaga agaactatta agagaaagaa aacgcattgg aacagtcgga     660
attgcttctt acgattatca ccaaggaagt ggaacatttc tgtttcaagc cggtagtgga     720
atttatcacg taaagatgg agggccacaa ggatttacgc aacaaccttt aaggcccaat     780
ctagtggaaa ctagttgtcc caacatacgg atggatccaa attatgccc cgctgatcca     840
gactggattg cttttatca tagcaacgat atttggatat ctaacatcgt aaccagagaa     900
gaaaggagac tcacttatgt gcacaatgag ctagccaaca tggaagaaga tgccagatca     960
gctggagtcg ctacctttgt tctccaagaa gaatttgata gatattctgg ctattggtgg    1020
tgtccaaaag ctgaaacaac tcccagtggt ggtaaaattc ttagaattct atatgaagaa    1080
aatgatgaat ctgaggtgga aattattcat gttacatccc ctatgttgga acaaggagg    1140
gcagattcat tccgttatcc taaaacaggt acagcaaatc ctaaagtcac ttttaagatg    1200
tcagaaataa tgattgatgc tgaaggaagg atcatagatg tcatagataa ggaactaatt    1260
caaccttttg agattctatt tgaaggagtt gaatatattg ccagagctgg atggactcct    1320
gagggaaaat atgcttggtc catcctacta gatcgctccc agactcgcct acagatagtg    1380
ttgatctcac ctgaattatt tatcccagta gaagatgatg ttatggaaag gcagagactc    1440
attgagtcag tgcctgattc tgtgacgcca ctaattatct atgaagaaac aacagacatc    1500
tggataaata tccatgacat ctttcatgtt tttccccaaa gtcacgaaga ggaaattgag    1560
tttatttttg cctctgaatg caaaacaggt ttccgtcatt tatacaaaat tacatctatt    1620
ttaaaggaaa gcaaatataa acgatccagt ggtgggctgc ctgctccaag tgatttcaag    1680
tgtcctatca agaggagat agcaattacc agtggtgaat gggaagttct tggccggcat    1740
ggatctaata tccaagttga tgaagtcaga aggctggtat attttgaagg caccaaaagac    1800
tccccttttag agcatcacct gtacgtagtc agttacgtaa atcctggaga ggtgacaagg    1860
ctgactgacc gtggctactc acattcttgc tgcatcagtc agcactgtga cttctttata    1920
agtaagtata gtaaccagaa gaatccacac tgtgtgtccc tttacaagct atcaagtcct    1980
gaagatgacc caacttgcaa aacaaaggaa ttttgggcca ccattttgga ttcagcaggt    2040
cctcttcctg actatactcc tccagaaatt ttctcttttg aaagtactac tggatttaca    2100
```

-continued

```
ttgtatggga tgctctacaa gcctcatgat ctacagcctg gaaagaaata tcctactgtg    2160
ctgttcatat atggtggtcc tcaggtgcag ttggtgaata tcggtttaa aggagtcaag     2220 tatttccgct tgaataccct agcctctcta ggttatgtgg ttgtagtgat agacaacagg    2280
ggatcctgtc accgagggct aaatttgaa ggcgccttta aatataaaat gggtcaaata    2340
gaaattgacg atcaggtgga aggactccaa tatctagctt ctcgatatga tttcattgac    2400
ttagatcgtg tgggcatcca cggctggtcc tatggaggat acctctccct gatggcatta    2460
atgcagaggt cagatatctt cagggttgct attgctgggg ccccagtcac tctgtggatc    2520
ttctatgata caggatacac ggaacgttat atgggtcacc ctgaccagaa tgaacagggc    2580
tattacttag atctgtggc catgcaagca gaaaagttcc cctctgaacc aaatcgttta    2640
ctgctcttac atggtttcct ggatgagaat gtccattttg cacataccag tatattactg    2700
agttttttag tgagggctgg aaagccatat gatttacaga tctatcctca ggagagacac    2760
agcataagag ttcctgaatc gggagaacat tatgaactgc atcttttgca ctaccttcaa    2820
gaaaaccttg gatcacgtat tgctgctcta aaagtgatat aattttgacc tgtgtagaac    2880
tctctggtat acactggcta tttaaccaaa tgaggaggtt taatcaacag aaaacacaga    2940
attgatcatc acattttgat acctgccatg taacatctac tcctgaaaat aaatgtggtg    3000
ccatgcaggg gtctacggtt tgtggtagta atctaatacc ttaaccccac atgctcaaaa    3060
tcaaatgata catattcctg agagacccag caataccata agaattacta aaaaaaaaaa    3120
```

<210> SEQ ID NO 6
<211> LENGTH: 882
<212> TYPE: PRT
<213> ORGANISM: Homo sapiens

<400> SEQUENCE: 6

```
Met Ala Ala Ala Met Glu Thr Glu Gln Leu Gly Val Glu Ile Phe Glu
1               5                   10                  15

Thr Ala Asp Cys Glu Glu Asn Ile Glu Ser Gln Asp Arg Pro Lys Leu
            20                  25                  30

Glu Pro Phe Tyr Val Glu Arg Tyr Ser Trp Ser Gln Leu Lys Lys Leu
        35                  40                  45

Leu Ala Asp Thr Arg Lys Tyr His Gly Tyr Met Met Ala Lys Ala Pro
    50                  55                  60

His Asp Phe Met Phe Val Lys Arg Asn Asp Pro Asp Gly Pro His Ser
65                  70                  75                  80

Asp Arg Ile Tyr Tyr Leu Ala Met Ser Gly Glu Asn Arg Glu Asn Thr
                85                  90                  95

Leu Phe Tyr Ser Glu Ile Pro Lys Thr Ile Asn Arg Ala Ala Val Leu
            100                 105                 110

Met Leu Ser Trp Lys Pro Leu Leu Asp Leu Phe Gln Ala Thr Leu Asp
        115                 120                 125

Tyr Gly Met Tyr Ser Arg Glu Glu Leu Leu Arg Glu Arg Lys Arg
    130                 135                 140

Ile Gly Thr Val Gly Ile Ala Ser Tyr Asp Tyr His Gln Gly Ser Gly
145                 150                 155                 160

Thr Phe Leu Phe Gln Ala Gly Ser Gly Ile Tyr His Val Lys Asp Gly
                165                 170                 175

Gly Pro Gln Gly Phe Thr Gln Gln Pro Leu Arg Pro Asn Leu Val Glu
            180                 185                 190

Thr Ser Cys Pro Asn Ile Arg Met Asp Pro Lys Leu Cys Pro Ala Asp
```

```
            195                 200                 205
Pro Asp Trp Ile Ala Phe Ile His Ser Asn Asp Ile Trp Ile Ser Asn
210                     215                 220

Ile Val Thr Arg Glu Glu Arg Leu Thr Tyr Val His Asn Glu Leu
225                 230                 235                 240

Ala Asn Met Glu Glu Asp Ala Arg Ser Ala Gly Val Ala Thr Phe Val
                245                 250                 255

Leu Gln Glu Glu Phe Asp Arg Tyr Ser Gly Tyr Trp Trp Cys Pro Lys
                260                 265                 270

Ala Glu Thr Thr Pro Ser Gly Gly Lys Ile Leu Arg Ile Leu Tyr Glu
                275                 280                 285

Glu Asn Asp Glu Ser Glu Val Glu Ile Ile His Val Thr Ser Pro Met
290                     295                 300

Leu Glu Thr Arg Arg Ala Asp Ser Phe Arg Tyr Pro Lys Thr Gly Thr
305                     310                 315                 320

Ala Asn Pro Lys Val Thr Phe Lys Met Ser Glu Ile Met Ile Asp Ala
                325                 330                 335

Glu Gly Arg Ile Ile Asp Val Ile Asp Lys Glu Leu Ile Gln Pro Phe
                340                 345                 350

Glu Ile Leu Phe Glu Gly Val Glu Tyr Ile Ala Arg Ala Gly Trp Thr
                355                 360                 365

Pro Glu Gly Lys Tyr Ala Trp Ser Ile Leu Leu Asp Arg Ser Gln Thr
                370                 375                 380

Arg Leu Gln Ile Val Leu Ile Ser Pro Glu Leu Phe Ile Pro Val Glu
385                     390                 395                 400

Asp Asp Val Met Glu Arg Gln Arg Leu Ile Glu Ser Val Pro Asp Ser
                405                 410                 415

Val Thr Pro Leu Ile Ile Tyr Glu Glu Thr Thr Asp Ile Trp Ile Asn
                420                 425                 430

Ile His Asp Ile Phe His Val Phe Pro Gln Ser His Glu Glu Ile
                435                 440                 445

Glu Phe Ile Phe Ala Ser Glu Cys Lys Thr Gly Phe Arg His Leu Tyr
                450                 455                 460

Lys Ile Thr Ser Ile Leu Lys Glu Ser Lys Tyr Lys Arg Ser Gly
465                     470                 475                 480

Gly Leu Pro Ala Pro Ser Asp Phe Lys Cys Pro Ile Lys Glu Glu Ile
                485                 490                 495

Ala Ile Thr Ser Gly Glu Trp Glu Val Leu Gly Arg His Gly Ser Asn
                500                 505                 510

Ile Gln Val Asp Glu Val Arg Arg Leu Val Tyr Phe Glu Gly Thr Lys
                515                 520                 525

Asp Ser Pro Leu Glu His His Leu Tyr Val Val Ser Tyr Val Asn Pro
530                     535                 540

Gly Glu Val Thr Arg Leu Thr Asp Arg Gly Tyr Ser His Ser Cys Cys
545                     550                 555                 560

Ile Ser Gln His Cys Asp Phe Phe Ile Ser Lys Tyr Ser Asn Gln Lys
                565                 570                 575

Asn Pro His Cys Val Ser Leu Tyr Lys Leu Ser Ser Pro Glu Asp Asp
                580                 585                 590

Pro Thr Cys Lys Thr Lys Glu Phe Trp Ala Thr Ile Leu Asp Ser Ala
                595                 600                 605

Gly Pro Leu Pro Asp Tyr Thr Pro Pro Glu Ile Phe Ser Phe Glu Ser
                610                 615                 620
```

```
Thr Thr Gly Phe Thr Leu Tyr Gly Met Leu Tyr Lys Pro His Asp Leu
625                 630                 635                 640

Gln Pro Gly Lys Lys Tyr Pro Thr Val Leu Phe Ile Tyr Gly Gly Pro
                645                 650                 655

Gln Val Gln Leu Val Asn Asn Arg Phe Lys Gly Val Lys Tyr Phe Arg
                660                 665                 670

Leu Asn Thr Leu Ala Ser Leu Gly Tyr Val Val Val Ile Asp Asn
                675                 680                 685

Arg Gly Ser Cys His Arg Gly Leu Lys Phe Glu Gly Ala Phe Lys Tyr
690                 695                 700

Lys Met Gly Gln Ile Glu Ile Asp Asp Gln Val Glu Gly Leu Gln Tyr
705                 710                 715                 720

Leu Ala Ser Arg Tyr Asp Phe Ile Asp Leu Asp Arg Val Gly Ile His
                725                 730                 735

Gly Trp Ser Tyr Gly Gly Tyr Leu Ser Leu Met Ala Leu Met Gln Arg
                740                 745                 750

Ser Asp Ile Phe Arg Val Ala Ile Ala Gly Ala Pro Val Thr Leu Trp
                755                 760                 765

Ile Phe Tyr Asp Thr Gly Tyr Thr Glu Arg Tyr Met Gly His Pro Asp
770                 775                 780

Gln Asn Glu Gln Gly Tyr Tyr Leu Gly Ser Val Ala Met Gln Ala Glu
785                 790                 795                 800

Lys Phe Pro Ser Glu Pro Asn Arg Leu Leu Leu Leu His Gly Phe Leu
                805                 810                 815

Asp Glu Asn Val His Phe Ala His Thr Ser Ile Leu Leu Ser Phe Leu
                820                 825                 830

Val Arg Ala Gly Lys Pro Tyr Asp Leu Gln Ile Tyr Pro Gln Glu Arg
                835                 840                 845

His Ser Ile Arg Val Pro Glu Ser Gly Glu His Tyr Glu Leu His Leu
                850                 855                 860

Leu His Tyr Leu Gln Glu Asn Leu Gly Ser Arg Ile Ala Ala Leu Lys
865                 870                 875                 880

Val Ile

<210> SEQ ID NO 7
<211> LENGTH: 830
<212> TYPE: PRT
<213> ORGANISM: Homo sapiens

<400> SEQUENCE: 7

Leu Arg Ser Ile Ile His Gly Ser Arg Lys Tyr Ser Gly Leu Ile Val
1               5                   10                  15

Asn Lys Ala Pro His Asp Phe Gln Phe Val Gln Lys Thr Asp Glu Ser
                20                  25                  30

Gly Pro His Ser His Arg Leu Tyr Tyr Leu Gly Met Pro Tyr Gly Ser
                35                  40                  45

Arg Glu Asn Ser Leu Leu Tyr Ser Glu Ile Pro Lys Lys Val Arg Lys
                50                  55                  60

Glu Ala Leu Leu Leu Leu Ser Trp Lys Gln Met Leu Asp His Phe Gln
65                  70                  75                  80

Ala Thr Pro His His Gly Val Tyr Ser Arg Glu Glu Leu Leu Arg
                85                  90                  95

Glu Arg Lys Arg Leu Gly Val Phe Gly Ile Thr Ser Tyr Asp Phe His
                100                 105                 110
```

```
Ser Glu Ser Gly Leu Phe Leu Phe Gln Ala Ser Asn Ser Leu Phe His
    115                 120                 125

Cys Arg Asp Gly Gly Lys Asn Gly Phe Met Val Ser Pro Met Lys Pro
    130                 135                 140

Leu Glu Ile Lys Thr Gln Cys Ser Gly Pro Arg Met Asp Pro Lys Ile
145                 150                 155                 160

Cys Pro Ala Asp Pro Ala Phe Phe Ser Phe Asn Asn Ser Asp Leu
                165                 170                 175

Trp Val Ala Asn Ile Glu Thr Gly Glu Arg Arg Leu Thr Phe Cys
                180                 185                 190

His Gln Gly Leu Ser Asn Val Leu Asp Asp Pro Lys Ser Ala Gly Val
    195                 200                 205

Ala Thr Phe Val Ile Gln Glu Glu Phe Asp Arg Phe Thr Gly Tyr Trp
    210                 215                 220

Trp Cys Pro Thr Ala Ser Trp Glu Gly Ser Gln Gly Leu Lys Thr Leu
225                 230                 235                 240

Arg Ile Leu Tyr Glu Glu Val Asp Glu Ser Glu Val Glu Val Ile His
                245                 250                 255

Val Pro Ser Pro Ala Leu Glu Glu Arg Lys Thr Asp Ser Tyr Arg Tyr
            260                 265                 270

Pro Arg Thr Gly Ser Lys Asn Pro Lys Ile Ala Leu Lys Leu Ala Glu
        275                 280                 285

Phe Gln Thr Asp Ser Gln Gly Lys Ile Val Ser Thr Gln Glu Lys Glu
    290                 295                 300

Leu Val Gln Pro Phe Ser Ser Leu Phe Pro Lys Val Glu Tyr Ile Ala
305                 310                 315                 320

Arg Ala Gly Trp Thr Arg Asp Gly Lys Tyr Ala Trp Ala Met Phe Leu
                325                 330                 335

Asp Arg Pro Gln Gln Trp Leu Gln Leu Val Leu Pro Pro Ala Leu
            340                 345                 350

Phe Ile Pro Ser Thr Glu Asn Glu Glu Gln Arg Leu Ala Ser Ala Arg
    355                 360                 365

Ala Val Pro Arg Asn Val Gln Pro Tyr Val Val Tyr Glu Glu Val Thr
    370                 375                 380

Asn Val Trp Ile Asn Val His Asp Ile Phe Tyr Pro Phe Pro Gln Ser
385                 390                 395                 400

Glu Gly Glu Asp Glu Leu Cys Phe Leu Arg Ala Asn Glu Cys Lys Thr
                405                 410                 415

Gly Phe Cys His Leu Tyr Lys Val Thr Ala Val Leu Lys Ser Gln Gly
            420                 425                 430

Tyr Asp Trp Ser Glu Pro Phe Ser Pro Gly Glu Asp Glu Phe Lys Cys
        435                 440                 445

Pro Ile Lys Glu Glu Ile Ala Leu Thr Ser Gly Glu Trp Glu Val Leu
    450                 455                 460

Ala Arg His Gly Ser Lys Ile Trp Val Asn Glu Glu Thr Lys Leu Val
465                 470                 475                 480

Tyr Phe Gln Gly Thr Lys Asp Thr Pro Leu Glu His His Leu Tyr Val
                485                 490                 495

Val Ser Tyr Glu Ala Ala Gly Glu Ile Val Arg Leu Thr Thr Pro Gly
            500                 505                 510

Phe Ser His Ser Cys Ser Met Ser Gln Asn Phe Asp Met Phe Val Ser
        515                 520                 525
```

-continued

```
His Tyr Ser Ser Val Ser Thr Pro Pro Cys Val His Val Tyr Lys Leu
    530                 535                 540

Ser Gly Pro Asp Asp Asp Pro Leu His Lys Gln Pro Arg Phe Trp Ala
545                 550                 555                 560

Ser Met Met Glu Ala Ala Ser Cys Pro Pro Asp Tyr Val Pro Pro Glu
                565                 570                 575

Ile Phe His Phe His Thr Arg Ser Asp Val Arg Leu Tyr Gly Met Ile
            580                 585                 590

Tyr Lys Pro His Ala Leu Gln Pro Gly Lys Lys His Pro Thr Val Leu
        595                 600                 605

Phe Val Tyr Gly Gly Pro Gln Val Gln Leu Val Asn Asn Ser Phe Lys
    610                 615                 620

Gly Ile Lys Tyr Leu Arg Leu Asn Thr Leu Ala Ser Leu Gly Tyr Ala
625                 630                 635                 640

Val Val Val Ile Asp Gly Arg Gly Ser Cys Gln Arg Gly Leu Arg Phe
                645                 650                 655

Glu Gly Ala Leu Lys Asn Gln Met Gly Gln Val Glu Ile Glu Asp Gln
            660                 665                 670

Val Glu Gly Leu Gln Phe Val Ala Glu Lys Tyr Gly Phe Ile Asp Leu
        675                 680                 685

Ser Arg Val Ala Ile His Gly Trp Ser Tyr Gly Gly Phe Leu Ser Leu
    690                 695                 700

Met Gly Leu Ile His Lys Pro Gln Val Phe Lys Val Ala Ile Ala Gly
705                 710                 715                 720

Ala Pro Val Thr Val Trp Met Ala Tyr Asp Thr Gly Tyr Thr Glu Arg
                725                 730                 735

Tyr Met Asp Val Pro Glu Asn Asn Gln His Gly Tyr Glu Ala Gly Ser
            740                 745                 750

Val Ala Leu His Val Glu Lys Leu Pro Asn Glu Pro Asn Arg Leu Leu
        755                 760                 765

Ile Leu His Gly Phe Leu Asp Glu Asn Val His Phe Phe His Thr Asn
    770                 775                 780

Phe Leu Val Ser Gln Leu Ile Arg Ala Gly Lys Pro Tyr Gln Leu Gln
785                 790                 795                 800

Ile Tyr Pro Asn Glu Arg His Ser Ile Arg Cys Pro Glu Ser Gly Glu
                805                 810                 815

His Tyr Glu Val Thr Leu Leu His Phe Leu Gln Glu Tyr Leu
            820                 825                 830

<210> SEQ ID NO 8
<211> LENGTH: 2495
<212> TYPE: DNA
<213> ORGANISM: Homo sapiens

<400> SEQUENCE: 8
ctccggagca tcatccacgg cagccgcaag tactcgggcc tcattgtcaa caaggcgccc      60
cacgacttcc agtttgtgca gaagacggat gagtctgggc cccactccca ccgcctctac     120
tacctgggaa tgccatatgg cagccgggag aactccctcc tctactctga gattcccaag     180
aaggtccgga aagaggctct gctgctcctg tcctggaagc agatgctgga tcatttccag     240

gccacgcccc accatggggt ctactctcgg gaggaggagc tgctgaggga gcggaaacgc     300
ctgggggtct tcggcatcac ctcctacgac ttccacagcg agagtggcct cttcctcttc     360
caggccagca acagcctctt ccactgccgc gacggcggca agaacggctt catggtgtcc     420
```

| | |
|---|---|
| cctatgaaac cgctggaaat caagacccag tgctcagggc cccggatgga ccccaaaatc | 480 |
| tgccctgccg accctgcctt cttctccttc aacaataaca gcgacctgtg ggtggccaac | 540 |
| atcgagacag gcgaggagcg gcggctgacc ttctgccacc aaggtttatc caatgtcctg | 600 |
| gatgacccca gtctgcggg tgtggccacc ttcgtcatac aggaagagtt cgaccgcttc | 660 |
| actgggtact ggtggtgccc cacagcctcc tgggaaggtt cagagggcct caagacgctg | 720 |
| cgaatcctgt atgaggaagt cgatgagtcc gaggtggagg tcattcacgt ccctctcct | 780 |
| gcgctagaag aaaggaagac ggactcgtat cggtacccca ggacaggcag caagaatccc | 840 |
| aagattgcct tgaaactggc tgagttccag actgacagcc agggcaagat cgtctcgacc | 900 |
| caggagaagg agctggtgca gcccttcagc tcgctgttcc gaaggtgga gtacatcgcc | 960 |
| agggccgggt ggacccggga tggcaaatac gcctgggcca tgttcctgga ccggccccag | 1020 |
| cagtggctcc agctcgtcct cctcccccg gccctgttca tcccgagcac agagaatgag | 1080 |
| gagcagcggc tagcctctgc cagagctgtc cccaggaatg tccagccgta tgtggtgtac | 1140 |
| gaggaggtca ccaacgtctg gatcaatgtt catgacatct tctatccctt cccccaatca | 1200 |
| gagggagagg acgagctctg ctttctccgc gccaatgaat gcaagaccgg cttctgccat | 1260 |
| ttgtacaaag tcaccgccgt tttaaaatcc cagggctacg attggagtga gcccttcagc | 1320 |
| cccggggaag atgaatttaa gtgccccatt aaggaagaga ttgctctgac cagcggtgaa | 1380 |
| tgggaggttt tggcgaggca cggctccaag atctgggtca atgaggagac caagctggtg | 1440 |
| tacttccagg gcaccaagga cacgccgctg gagcaccacc tctacgtggt cagctatgag | 1500 |
| gcggccggcg agatcgtacg cctcaccacg cccggcttct cccatagctg ctccatgagc | 1560 |
| cagaacttcg acatgttcgt cagccactac agcagcgtga gcacgccgcc ctgcgtgcac | 1620 |
| gtctacaagc tgagcggccc cgacgacgac cccctgcaca agcagccccg cttctgggct | 1680 |
| agcatgatgg aggcagccag ctgccccccg gattatgttc ctccagagat cttccatttc | 1740 |
| cacacgcgct cggatgtgcg gctctacggc atgatctaca agccccacgc cttgcagcca | 1800 |
| gggaagaagc accccaccgt cctctttgta tatggaggcc cccaggtgca gctggtgaat | 1860 |
| aactccttca aaggcatcaa gtacttgcgg ctcaacacac tggcctccct gggctacgcc | 1920 |
| gtggttgtga ttgacggcag gggctcctgt cagcgagggc ttcggttcga aggggccctg | 1980 |
| aaaaaccaaa tgggccaggt ggagatcgag gaccaggtgg agggcctgca gttcgtggcc | 2040 |
| gagaagtatg gcttcatcga cctgagccga gttgccatcc atggctggtc ctacggggc | 2100 |
| ttcctctcgc tcatggggct aatccacaag ccccaggtgt tcaaggtggc catcgcgggt | 2160 |
| gccccggtca ccgtctggat ggcctacgac acagggtaca ctgagcgcta catggacgtc | 2220 |
| cctgagaaca accagcacgg ctatgaggcg ggttccgtgg ccctgcacgt ggagaagctg | 2280 |
| cccaatgagc ccaaccgctt gcttatcctc cacggcttcc tggacgaaaa cgtgcacttt | 2340 |
| ttccacacaa acttcctcgt ctcccaactg atccgagcag ggaaaccttg ccagctccag | 2400 |
| atctacccca acgagagaca cagtattcgc tgccccgagt cgggcgagca ctatgaagtc | 2460 |
| acgttactgc actttctaca ggaataccte tgagc | 2495 |

<210> SEQ ID NO 9
<211> LENGTH: 813
<212> TYPE: PRT
<213> ORGANISM: Artificial sequence
<220> FEATURE:
<223> OTHER INFORMATION: GDD protein sequence

<400> SEQUENCE: 9

```
Ser Trp Asp Gly Leu Arg Ser Ile Ile His Gly Ser Arg Lys Tyr Ser
1               5                   10                  15

Gly Leu Ile Val Asn Lys Ala Pro His Asp Phe Gln Phe Val Gln Lys
            20                  25                  30

Thr Asp Glu Ser Gly Pro His Ser His Arg Leu Tyr Tyr Leu Gly Met
        35                  40                  45

Pro Tyr Gly Ser Arg Glu Asn Ser Leu Leu Tyr Ser Glu Ile Pro Lys
    50                  55                  60

Lys Val Arg Lys Glu Ala Leu Leu Leu Ser Trp Lys Gln His Leu
65              70                  75                  80

Asp His Phe Gln Ala Thr Pro His His Gly Val Tyr Ser Arg Glu Glu
                85                  90                  95

Glu Leu Leu Arg Glu Arg Lys Arg Leu Gly Val Phe Gly Ile Thr Ser
            100                 105                 110

Tyr Asp Phe His Ser Glu Ser Gly Leu Phe Leu Phe Gln Ala Ser Asn
        115                 120                 125

Ser Leu Phe His Cys Arg Asp Gly Gly Lys Asn Gly Phe Met Val Ser
130                 135                 140

Pro Gly Pro Gly Cys Val Ser Pro Met Lys Pro Leu Glu Ile Lys Thr
145                 150                 155                 160

Gln Cys Ser Gly Pro Arg Met Asp Pro Lys Ile Cys Pro Ala Asp Pro
                165                 170                 175

Ala Phe Phe Ser Phe Ile Asn Asn Ser Asp Leu Trp Val Ala Asn Ile
            180                 185                 190

Glu Thr Gly Glu Glu Arg Arg Leu Thr Phe Cys His Gln Gly Leu Ser
        195                 200                 205

Asn Val Leu Asp Asp Pro Lys Ser Ala Gly Val Ala Thr Phe Val Ile
    210                 215                 220

Gln Glu Glu Phe Asp Arg Phe Thr Gly Tyr Trp Trp Cys Pro Thr Ala
225                 230                 235                 240

Ser Trp Glu Glu Gly Leu Lys Thr Leu Arg Ile Leu Tyr Glu Glu Val
                245                 250                 255

Asp Glu Ser Glu Val Glu Val Ile His Val Pro Ser Pro Ala Leu Glu
            260                 265                 270

Glu Arg Lys Thr Asp Ser Tyr Arg Tyr Pro Arg Thr Gly Ser Lys Asn
        275                 280                 285

Pro Lys Ile Ala Leu Lys Leu Ala Glu Phe Gln Thr Asp Ser Gln Gly
    290                 295                 300

Lys Ile Val Ser Thr Gln Glu Lys Glu Leu Val Gln Pro Phe Ser Ser
305                 310                 315                 320

Leu Phe Pro Lys Val Glu Tyr Ile Ala Arg Ala Gly Ala Trp Ala Met
                325                 330                 335

Phe Leu Asp Arg Pro Gln Gln Trp Leu Gln Leu Val Leu Leu Pro Pro
            340                 345                 350

Ala Leu Phe Ile Pro Ser Thr Glu Asn Glu Glu Gln Arg Leu Ala Ser
        355                 360                 365

Ala Arg Ala Val Pro Arg Asn Val Gln Pro Tyr Val Val Tyr Glu Glu
    370                 375                 380

Val Thr Asn Val Trp Ile Asn Val His Asp Ile Phe Tyr Pro Phe Pro
385                 390                 395                 400

Gln Ser Glu Gly Glu Asp Glu Leu Cys Phe Leu Arg Ala Asn Glu Cys
                405                 410                 415
```

```
Lys Thr Gly Phe Cys His Leu Tyr Lys Val Thr Ala Val Leu Lys Ser
            420                 425                 430

Gln Gly Tyr Asp Trp Ser Glu Pro Phe Ser Pro Gly Glu Gly Glu Gln
        435                 440                 445

Ser Leu Thr Asn Ala Ile Trp Val Asn Glu Thr Lys Leu Val Tyr
    450                 455                 460

Phe Gln Gly Thr Lys Asp Thr Pro Leu Glu His His Leu Tyr Val Val
465                 470                 475                 480

Ser Tyr Glu Ala Ala Gly Glu Ile Val Arg Leu Thr Thr Pro Gly Phe
                485                 490                 495

Ser His Ser Cys Ser Met Ser Gln Asn Phe Asp Met Phe Val Ser His
            500                 505                 510

Tyr Ser Ser Val Ser Thr Pro Pro Cys Val His Val Tyr Lys Leu Ser
        515                 520                 525

Gly Pro Asp Asp Pro Leu His Lys Gln Pro Arg Phe Trp Ala Ser
530                 535                 540

Met Met Glu Ala Ala Lys Ile Phe His Phe His Thr Arg Ser Asp Val
545                 550                 555                 560

Arg Leu Tyr Gly Met Ile Tyr Lys Pro His Ala Leu Gln Pro Gly Lys
                565                 570                 575

Lys His Pro Thr Val Leu Phe Val Tyr Gly Gly Pro Gln Val Gln Leu
            580                 585                 590

Val Asn Asn Ser Phe Lys Gly Ile Lys Tyr Leu Arg Leu Asn Thr Leu
        595                 600                 605

Ala Ser Leu Gly Tyr Ala Val Val Ile Asp Gly Arg Gly Ser Cys
    610                 615                 620

Gln Arg Gly Leu Arg Phe Glu Gly Ala Leu Lys Asn Gln Met Gly Gln
625                 630                 635                 640

Val Glu Ile Glu Asp Gln Val Glu Gly Leu Gln Phe Val Ala Glu Lys
                645                 650                 655

Tyr Gly Phe Ile Asp Leu Ser Arg Val Ala Ile His Gly Trp Ser Tyr
            660                 665                 670

Gly Gly Phe Leu Ser Leu Met Gly Leu Ile His Lys Pro Gln Val Phe
        675                 680                 685

Lys Val Ala Ile Ala Gly Ala Pro Val Thr Val Trp Met Ala Tyr Asp
    690                 695                 700

Thr Gly Tyr Thr Glu Arg Tyr Met Asp Val Pro Glu Asn Asn Gln His
705                 710                 715                 720

Gly Tyr Glu Ala Gly Ser Val Ala Leu His Val Glu Lys Leu Pro Asn
                725                 730                 735

Glu Pro Asn Arg Leu Leu Ile Leu His Gly Phe Leu Asp Glu Asn Val
            740                 745                 750

His Phe Phe His Thr Asn Phe Leu Val Ser Gln Leu Ile Arg Ala Gly
        755                 760                 765

Lys Pro Tyr Gln Leu Gln Val Ala Leu Pro Pro Val Ser Pro Gln Ile
    770                 775                 780

Tyr Pro Asn Glu Arg His Ser Ile Arg Cys Pro Glu Ser Gly Glu His
785                 790                 795                 800

Tyr Glu Val Thr Leu Leu His Phe Leu Gln Glu Tyr Leu
                805                 810

<210> SEQ ID NO 10
<211> LENGTH: 766
<212> TYPE: PRT
```

<213> ORGANISM: Homo sapiens

<400> SEQUENCE: 10

```
Met Lys Thr Pro Trp Lys Val Leu Leu Gly Leu Leu Ala Ala Ala
1               5                   10                  15

Leu Val Thr Ile Ile Thr Val Pro Val Val Leu Leu Asn Lys Gly Thr
            20                  25                  30

Asp Asp Ala Thr Ala Asp Ser Arg Lys Thr Tyr Thr Leu Thr Asp Tyr
        35                  40                  45

Leu Lys Asn Thr Tyr Arg Leu Lys Leu Tyr Ser Leu Arg Trp Ile Ser
50                  55                  60

Asp His Glu Tyr Leu Tyr Lys Gln Glu Asn Asn Ile Leu Val Phe Asn
65                  70                  75                  80

Ala Glu Tyr Gly Asn Ser Ser Val Phe Leu Glu Asn Ser Thr Phe Asp
                85                  90                  95

Glu Phe Gly His Ser Ile Asn Asp Tyr Ser Ile Ser Pro Asp Gly Gln
            100                 105                 110

Phe Ile Leu Leu Glu Tyr Asn Tyr Val Lys Gln Trp Arg His Ser Tyr
        115                 120                 125

Thr Ala Ser Tyr Asp Ile Tyr Asp Leu Asn Lys Arg Gln Leu Ile Thr
    130                 135                 140

Glu Glu Arg Ile Pro Asn Asn Thr Gln Trp Val Thr Trp Ser Pro Val
145                 150                 155                 160

Gly His Lys Leu Ala Tyr Val Trp Asn Asn Asp Ile Tyr Val Lys Ile
                165                 170                 175

Glu Pro Asn Leu Pro Ser Tyr Arg Ile Thr Trp Thr Gly Lys Glu Asp
            180                 185                 190

Ile Ile Tyr Asn Gly Ile Thr Asp Trp Val Tyr Glu Glu Glu Val Phe
        195                 200                 205

Ser Ala Tyr Ser Ala Leu Trp Trp Ser Pro Asn Gly Thr Phe Leu Ala
    210                 215                 220

Tyr Ala Gln Phe Asn Asp Thr Glu Val Pro Leu Ile Glu Tyr Ser Phe
225                 230                 235                 240

Tyr Ser Asp Glu Ser Leu Gln Tyr Pro Lys Thr Val Arg Val Pro Tyr
                245                 250                 255

Pro Lys Ala Gly Ala Val Asn Pro Thr Val Lys Phe Phe Val Val Asn
            260                 265                 270

Thr Asp Ser Leu Ser Ser Val Thr Asn Ala Thr Ser Ile Gln Ile Thr
        275                 280                 285

Ala Pro Ala Ser Met Leu Ile Gly Asp His Tyr Leu Cys Asp Val Thr
    290                 295                 300

Trp Ala Thr Gln Glu Arg Ile Ser Leu Gln Trp Leu Arg Arg Ile Gln
305                 310                 315                 320

Asn Tyr Ser Val Met Asp Ile Cys Asp Tyr Asp Glu Ser Ser Gly Arg
                325                 330                 335

Trp Asn Cys Leu Val Ala Arg Gln His Ile Glu Met Ser Thr Thr Gly
            340                 345                 350

Trp Val Gly Arg Phe Arg Pro Ser Glu Pro His Phe Thr Leu Asp Gly
        355                 360                 365

Asn Ser Phe Tyr Lys Ile Ile Ser Asn Glu Glu Gly Tyr Arg His Ile
    370                 375                 380

Cys Tyr Phe Gln Ile Asp Lys Lys Asp Cys Thr Phe Ile Thr Lys Gly
385                 390                 395                 400
```

```
Thr Trp Glu Val Ile Gly Ile Glu Ala Leu Thr Ser Asp Tyr Leu Tyr
            405                 410                 415
Tyr Ile Ser Asn Glu Tyr Lys Gly Met Pro Gly Gly Arg Asn Leu Tyr
                420                 425                 430
Lys Ile Gln Leu Ser Asp Tyr Thr Lys Val Thr Cys Leu Ser Cys Glu
            435                 440                 445
Leu Asn Pro Glu Arg Cys Gln Tyr Tyr Ser Val Ser Phe Ser Lys Glu
450                 455                 460
Ala Lys Tyr Tyr Gln Leu Arg Cys Ser Gly Pro Gly Leu Pro Leu Tyr
465                 470                 475                 480
Thr Leu His Ser Ser Val Asn Asp Lys Gly Leu Arg Val Leu Glu Asp
                485                 490                 495
Asn Ser Ala Leu Asp Lys Met Leu Gln Asn Val Gln Met Pro Ser Lys
            500                 505                 510
Lys Leu Asp Phe Ile Ile Leu Asn Glu Thr Lys Phe Trp Tyr Gln Met
            515                 520                 525
Ile Leu Pro Pro His Phe Asp Lys Ser Lys Lys Tyr Pro Leu Leu Leu
            530                 535                 540
Asp Val Tyr Ala Gly Pro Cys Ser Gln Lys Ala Asp Thr Val Phe Arg
545                 550                 555                 560
Leu Asn Trp Ala Thr Tyr Leu Ala Ser Thr Glu Asn Ile Ile Val Ala
                565                 570                 575
Ser Phe Asp Gly Arg Gly Ser Gly Tyr Gln Gly Asp Lys Ile Met His
            580                 585                 590
Ala Ile Asn Arg Arg Leu Gly Thr Phe Glu Val Glu Asp Gln Ile Glu
            595                 600                 605
Ala Ala Arg Gln Phe Ser Lys Met Gly Phe Val Asp Asn Lys Arg Ile
            610                 615                 620
Ala Ile Trp Gly Trp Ser Tyr Gly Gly Tyr Val Thr Ser Met Val Leu
625                 630                 635                 640
Gly Ser Gly Ser Gly Val Phe Lys Cys Gly Ile Ala Val Ala Pro Val
                645                 650                 655
Ser Arg Trp Glu Tyr Tyr Asp Ser Val Tyr Thr Glu Arg Tyr Met Gly
            660                 665                 670
Leu Pro Thr Pro Glu Asp Asn Leu Asp His Tyr Arg Asn Ser Thr Val
            675                 680                 685
Met Ser Arg Ala Glu Asn Phe Lys Gln Val Glu Tyr Leu Leu Ile His
            690                 695                 700
Gly Thr Ala Asp Asp Asn Val His Phe Gln Gln Ser Ala Gln Ile Ser
705                 710                 715                 720
Lys Ala Leu Val Asp Val Gly Val Asp Phe Gln Ala Met Trp Tyr Thr
                725                 730                 735
Asp Glu Asp His Gly Ile Ala Ser Ser Thr Ala His Gln His Ile Tyr
            740                 745                 750
Thr His Met Ser His Phe Ile Lys Gln Cys Phe Ser Leu Pro
            755                 760                 765

<210> SEQ ID NO 11
<211> LENGTH: 760
<212> TYPE: PRT
<213> ORGANISM: Homo sapiens

<400> SEQUENCE: 11

Met Lys Thr Trp Val Lys Ile Val Phe Gly Val Ala Thr Ser Ala Val
1               5                   10                  15
```

-continued

```
Leu Ala Leu Leu Val Met Cys Ile Val Leu Arg Pro Ser Arg Val His
            20                  25                  30

Asn Ser Glu Glu Asn Thr Met Arg Ala Leu Thr Leu Lys Asp Ile Leu
        35                  40                  45

Asn Gly Thr Phe Ser Tyr Lys Thr Phe Pro Asn Trp Ile Ser Gly
    50                  55                  60

Gln Glu Tyr Leu His Gln Ser Ala Asp Asn Ile Val Leu Tyr Asn
65                  70                  75                  80

Ile Glu Thr Gly Gln Ser Tyr Thr Ile Leu Ser Asn Arg Thr Met Lys
                85                  90                  95

Ser Val Asn Ala Ser Asn Tyr Gly Leu Ser Pro Asp Arg Gln Phe Val
            100                 105                 110

Tyr Leu Glu Ser Asp Tyr Ser Lys Leu Trp Arg Tyr Ser Tyr Thr Ala
        115                 120                 125

Thr Tyr Tyr Ile Tyr Asp Leu Ser Asn Gly Glu Phe Val Arg Gly Asn
    130                 135                 140

Glu Leu Pro Arg Pro Ile Gln Tyr Leu Cys Trp Ser Pro Val Gly Ser
145                 150                 155                 160

Lys Leu Ala Tyr Val Tyr Gln Asn Asn Ile Tyr Leu Lys Gln Arg Pro
                165                 170                 175

Gly Asp Pro Pro Phe Gln Ile Thr Phe Asn Gly Arg Glu Asn Lys Ile
            180                 185                 190

Phe Asn Gly Ile Pro Asp Trp Val Tyr Glu Glu Met Leu Pro Thr
        195                 200                 205

Lys Tyr Ala Leu Trp Trp Ser Pro Asn Gly Lys Phe Leu Ala Tyr Ala
    210                 215                 220

Glu Phe Asn Asp Thr Asp Ile Pro Val Ile Ala Tyr Ser Tyr Tyr Gly
225                 230                 235                 240

Asp Glu Gln Tyr Pro Arg Thr Ile Asn Ile Pro Tyr Pro Lys Ala Gly
                245                 250                 255

Ala Lys Asn Pro Val Val Arg Ile Phe Ile Ile Asp Thr Thr Tyr Pro
            260                 265                 270

Ala Tyr Val Gly Pro Gln Glu Val Pro Val Pro Ala Met Ile Ala Ser
        275                 280                 285

Ser Asp Tyr Tyr Phe Ser Trp Leu Thr Trp Val Thr Asp Glu Arg Val
    290                 295                 300

Cys Leu Gln Trp Leu Lys Arg Val Gln Asn Val Ser Val Leu Ser Ile
305                 310                 315                 320

Cys Asp Phe Arg Glu Asp Trp Gln Thr Trp Asp Cys Pro Lys Thr Gln
                325                 330                 335

Glu His Ile Glu Glu Ser Arg Thr Gly Trp Ala Gly Gly Phe Phe Val
            340                 345                 350

Ser Arg Pro Val Phe Ser Tyr Asp Ala Ile Ser Tyr Tyr Lys Ile Phe
        355                 360                 365

Ser Asp Lys Asp Gly Tyr Lys His Ile His Tyr Ile Lys Asp Thr Val
    370                 375                 380

Glu Asn Ala Ile Gln Ile Thr Ser Gly Lys Trp Glu Ala Ile Asn Ile
385                 390                 395                 400

Phe Arg Val Thr Gln Asp Ser Leu Phe Tyr Ser Ser Asn Glu Phe Glu
                405                 410                 415

Glu Tyr Pro Gly Arg Arg Asn Ile Tyr Arg Ile Ser Ile Gly Ser Tyr
            420                 425                 430
```

-continued

```
Pro Pro Ser Lys Lys Cys Val Thr Cys His Leu Arg Lys Glu Arg Cys
        435                 440                 445

Gln Tyr Tyr Thr Ala Ser Phe Ser Asp Tyr Ala Lys Tyr Tyr Ala Leu
    450                 455                 460

Val Cys Tyr Gly Pro Gly Ile Pro Ile Ser Thr Leu His Asp Gly Arg
465                 470                 475                 480

Thr Asp Gln Glu Ile Lys Ile Leu Glu Glu Asn Lys Glu Leu Glu Asn
                485                 490                 495

Ala Leu Lys Asn Ile Gln Leu Pro Lys Glu Glu Ile Lys Lys Leu Glu
            500                 505                 510

Val Asp Glu Ile Thr Leu Trp Tyr Lys Met Ile Leu Pro Pro Gln Phe
        515                 520                 525

Asp Arg Ser Lys Lys Tyr Pro Leu Leu Ile Gln Val Tyr Gly Gly Pro
    530                 535                 540

Cys Ser Gln Ser Val Arg Ser Val Phe Ala Val Asn Trp Ile Ser Tyr
545                 550                 555                 560

Leu Ala Ser Lys Glu Gly Met Val Ile Ala Leu Val Asp Gly Arg Gly
                565                 570                 575

Thr Ala Phe Gln Gly Asp Lys Leu Leu Tyr Ala Val Tyr Arg Lys Leu
            580                 585                 590

Gly Val Tyr Glu Val Glu Asp Gln Ile Thr Ala Val Arg Lys Phe Ile
        595                 600                 605

Glu Met Gly Phe Ile Asp Glu Lys Arg Ile Ala Ile Trp Gly Trp Ser
    610                 615                 620

Tyr Gly Gly Tyr Val Ser Ser Leu Ala Leu Ala Ser Gly Thr Gly Leu
625                 630                 635                 640

Phe Lys Cys Gly Ile Ala Val Ala Pro Val Ser Ser Trp Glu Tyr Tyr
                645                 650                 655

Ala Ser Val Tyr Thr Glu Arg Phe Met Gly Leu Pro Thr Lys Asp Asp
            660                 665                 670

Asn Leu Glu His Tyr Lys Asn Ser Thr Val Met Ala Arg Ala Glu Tyr
        675                 680                 685

Phe Arg Asn Val Asp Tyr Leu Leu Ile His Gly Thr Ala Asp Asp Asn
    690                 695                 700

Val His Phe Gln Asn Ser Ala Gln Ile Ala Lys Ala Leu Val Asn Ala
705                 710                 715                 720

Gln Val Asp Phe Gln Ala Met Trp Tyr Ser Asp Gln Asn His Gly Leu
                725                 730                 735

Ser Gly Leu Ser Thr Asn His Leu Tyr Thr His Met Thr His Phe Leu
            740                 745                 750

Lys Gln Cys Phe Ser Leu Ser Asp
        755                 760

<210> SEQ ID NO 12
<211> LENGTH: 24
<212> TYPE: DNA
<213> ORGANISM: Artificial sequence
<220> FEATURE:
<223> OTHER INFORMATION: Forward primer for GDD pr 1f

<400> SEQUENCE: 12
gtggagatcg aggaccaggt ggag                                          24

<210> SEQ ID NO 13
<211> LENGTH: 24
<212> TYPE: DNA
```

```
<213> ORGANISM: Artificial sequence
<220> FEATURE:
<223> OTHER INFORMATION: Forward primer for GDD pr 2f

<400> SEQUENCE: 13
caaagtgagg aaaaatgcac tccg                                              24

<210> SEQ ID NO 14
<211> LENGTH: 24
<212> TYPE: DNA
<213> ORGANISM: Artificial sequence
<220> FEATURE:
<223> OTHER INFORMATION: Forward primer for GDD pr 2a

<400> SEQUENCE: 14
tgaggaaaaa tgcactccga gcag                                              24

<210> SEQ ID NO 15
<211> LENGTH: 24
<212> TYPE: DNA
<213> ORGANISM: Artificial sequence
<220> FEATURE:
<223> OTHER INFORMATION: Forward primer for GDD pr 3f

<400> SEQUENCE: 15
aaactggctg agttccagac tgac                                              24

<210> SEQ ID NO 16
<211> LENGTH: 24
<212> TYPE: DNA
<213> ORGANISM: Artificial sequence
<220> FEATURE:
<223> OTHER INFORMATION: Forward primer for GDD pr 5f

<400> SEQUENCE: 16
cggggaaggt gagcagagcc tgac                                              24

<210> SEQ ID NO 17
<211> LENGTH: 24
<212> TYPE: DNA
<213> ORGANISM: Artificial sequence
<220> FEATURE:
<223> OTHER INFORMATION: Forward primer for GDD pr 6f

<400> SEQUENCE: 17
agaagcaccc caccgtcctc tttg                                              24

<210> SEQ ID NO 18
<211> LENGTH: 24
<212> TYPE: DNA
<213> ORGANISM: Artificial sequence
<220> FEATURE:
<223> OTHER INFORMATION: Forward primer for GDD pr 11f

<400> SEQUENCE: 18
gagaaggagc tggtgcagcc cttc                                              24

<210> SEQ ID NO 19
<211> LENGTH: 24
<212> TYPE: DNA
<213> ORGANISM: Artificial sequence
<220> FEATURE:
<223> OTHER INFORMATION: Forward primer for GDD pr 12f

<400> SEQUENCE: 19
tcagagggag aggacgagct ctgc                                              24
```

<210> SEQ ID NO 20
<211> LENGTH: 24
<212> TYPE: DNA
<213> ORGANISM: Artificial sequence
<220> FEATURE:
<223> OTHER INFORMATION: Forward primer for GDD pr 14f

<400> SEQUENCE: 20
ccgcttccag gtgcagaagc actc                                              24

<210> SEQ ID NO 21
<211> LENGTH: 24
<212> TYPE: DNA
<213> ORGANISM: Artificial sequence
<220> FEATURE:
<223> OTHER INFORMATION: Forward primer for GDD pr 15f

<400> SEQUENCE: 21
ctacgacttc cacagcgaga gtgg                                              24

<210> SEQ ID NO 22
<211> LENGTH: 25
<212> TYPE: DNA
<213> ORGANISM: Artificial sequence
<220> FEATURE:
<223> OTHER INFORMATION: Forward primer for GDD pr 16f

<400> SEQUENCE: 22
gatgagtccg aggtggaggt cattc                                             25

<210> SEQ ID NO 23
<211> LENGTH: 24
<212> TYPE: DNA
<213> ORGANISM: Artificial sequence
<220> FEATURE:
<223> OTHER INFORMATION: Reverse primer for GDD pr 1r

<400> SEQUENCE: 23
gctcagaggt attcctgtag aaag                                              24

<210> SEQ ID NO 24
<211> LENGTH: 24
<212> TYPE: DNA
<213> ORGANISM: Artificial sequence
<220> FEATURE:
<223> OTHER INFORMATION: Reverse primer for GDD pr 4r

<400> SEQUENCE: 24
cccatgttgg ccaggctggt cttg                                              24

<210> SEQ ID NO 25
<211> LENGTH: 24
<212> TYPE: DNA
<213> ORGANISM: Artificial sequence
<220> FEATURE:
<223> OTHER INFORMATION: Reverse primer for GDD pr 7r

<400> SEQUENCE: 25
aggaccagcc atggatggca actc                                              24

<210> SEQ ID NO 26
<211> LENGTH: 24
<212> TYPE: DNA
<213> ORGANISM: Artificial sequence
<220> FEATURE:

<223> OTHER INFORMATION: Reverse primer for GDD pr 8r

<400> SEQUENCE: 26
ccgctcagct tgtagacgtg cacg                                    24

<210> SEQ ID NO 27
<211> LENGTH: 24
<212> TYPE: DNA
<213> ORGANISM: Artificial sequence
<220> FEATURE:
<223> OTHER INFORMATION: Reverse primer for GDD pr 9r

<400> SEQUENCE: 27
tcattctctg tgctcgggat gaac                                    24

<210> SEQ ID NO 28
<211> LENGTH: 24
<212> TYPE: DNA
<213> ORGANISM: Artificial sequence
<220> FEATURE:
<223> OTHER INFORMATION: Reverse primer for GDD pr 13r

<400> SEQUENCE: 28
gcacatccga gcgcgtgtgg aaat                                    24

<210> SEQ ID NO 29
<211> LENGTH: 24
<212> TYPE: DNA
<213> ORGANISM: Artificial sequence
<220> FEATURE:
<223> OTHER INFORMATION: Reverse primer for GDD pr17r

<400> SEQUENCE: 29
tgggagaagc cgggcgtggt gagg                                    24

<210> SEQ ID NO 30
<211> LENGTH: 25
<212> TYPE: DNA
<213> ORGANISM: Artificial sequence
<220> FEATURE:
<223> OTHER INFORMATION: Reverse primer for GDD pr 18r

<400> SEQUENCE: 30
gcggtcgaac tcttcctgta tgacg                                   25

<210> SEQ ID NO 31
<211> LENGTH: 18
<212> TYPE: DNA
<213> ORGANISM: Artificial sequence
<220> FEATURE:
<223> OTHER INFORMATION: 5'RACE primer for GDD GSP 1.1

<400> SEQUENCE: 31
tgaaggagaa gaaggcag                                           18

<210> SEQ ID NO 32
<211> LENGTH: 24
<212> TYPE: DNA
<213> ORGANISM: Artificial sequence
<220> FEATURE:
<223> OTHER INFORMATION: 5'RACE primer for GDD GSP 2.1

<400> SEQUENCE: 32
cctgagcact gggtcttgat ttcc                                    24

```
<210> SEQ ID NO 33
<211> LENGTH: 36
<212> TYPE: DNA
<213> ORGANISM: Artificial sequence
<220> FEATURE:
<223> OTHER INFORMATION: 5' RACE Abridged Anchor Primer
<220> FEATURE:
<221> NAME/KEY: modified_base
<222> LOCATION: (24)..(24)
<223> OTHER INFORMATION: I inosine
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: modified_base
<222> LOCATION: (25)..(25)
<223> OTHER INFORMATION: I inosine
<220> FEATURE:
<221> NAME/KEY: modified_base
<222> LOCATION: (29)..(29)
<223> OTHER INFORMATION: I inosine
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: modified_base
<222> LOCATION: (30)..(30)
<223> OTHER INFORMATION: I inosine
<220> FEATURE:
<221> NAME/KEY: modified_base
<222> LOCATION: (34)..(34)
<223> OTHER INFORMATION: I inosine
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: modified_base
<222> LOCATION: (35)..(35)
<223> OTHER INFORMATION: I inosine

<400> SEQUENCE: 33
ggccacgcgt cgatcatgac gggnngggnn gggnng                                36

<210> SEQ ID NO 34
<211> LENGTH: 22
<212> TYPE: DNA
<213> ORGANISM: Artificial sequence
<220> FEATURE:
<223> OTHER INFORMATION: Primer DPP9 22F

<400> SEQUENCE: 34
gccggcgggt cccctgtgtc cg                                               22

<210> SEQ ID NO 35
<211> LENGTH: 24
<212> TYPE: DNA
<213> ORGANISM: Artificial sequence
<220> FEATURE:
<223> OTHER INFORMATION: primer GDD 3' end

<400> SEQUENCE: 35
gggcgggaca aagtgcctca ctgg                                             24

<210> SEQ ID NO 36
<211> LENGTH: 6
<212> TYPE: PRT
<213> ORGANISM: Artificial sequence
<220> FEATURE:
<223> OTHER INFORMATION: DPP4 serine recognition site
```

-continued

```
<400> SEQUENCE: 36

Gly Tyr Ser Trp Gly Gly
1               5

<210> SEQ ID NO 37
<211> LENGTH: 25
<212> TYPE: DNA
<213> ORGANISM: Artificial sequence
<220> FEATURE:
<223> OTHER INFORMATION: Met3f forward primer

<400> SEQUENCE: 37
ggctgagagg atggccacca ccggg                                          25

<210> SEQ ID NO 38
<211> LENGTH: 25
<212> TYPE: DNA
<213> ORGANISM: Artificial sequence
<220> FEATURE:
<223> OTHER INFORMATION: Primer mgdd pr 1F

<400> SEQUENCE: 38
acctgggagg aagcacccca ctgtg                                          25

<210> SEQ ID NO 39
<211> LENGTH: 22
<212> TYPE: DNA
<213> ORGANISM: Artificial sequence
<220> FEATURE:
<223> OTHER INFORMATION: Primer mgdd pr4F

<400> SEQUENCE: 39
ttccacctgg tcctcaatct cc                                             22

<210> SEQ ID NO 40
<211> LENGTH: 25
<212> TYPE: DNA
<213> ORGANISM: Artificial sequence
<220> FEATURE:
<223> OTHER INFORMATION: Forward primer mDPP9 1F

<400> SEQUENCE: 40
acctgggagg aagcacccca ctgtg                                          25

<210> SEQ ID NO 41
<211> LENGTH: 24
<212> TYPE: DNA
<213> ORGANISM: Artificial sequence
<220> FEATURE:
<223> OTHER INFORMATION: Reverse primer for mDPP9 2R

<400> SEQUENCE: 41
ctctccacat gcagggctac agac                                           24

<210> SEQ ID NO 42
<211> LENGTH: 9
<212> TYPE: PRT
<213> ORGANISM: Homo sapiens

<400> SEQUENCE: 42

Trp Gly Trp Ser Tyr Gly Gly Tyr Val
1               5

<210> SEQ ID NO 43
<211> LENGTH: 7
```

```
<212> TYPE: PRT
<213> ORGANISM: Homo sapiens

<400> SEQUENCE: 43

Ala Asp Asp Asn Val His Phe
1               5

<210> SEQ ID NO 44
<211> LENGTH: 7
<212> TYPE: PRT
<213> ORGANISM: Homo sapiens

<400> SEQUENCE: 44

Glu Asp His Gly Ile Ala Ser
1               5

<210> SEQ ID NO 45
<211> LENGTH: 7
<212> TYPE: PRT
<213> ORGANISM: Homo sapiens

<400> SEQUENCE: 45

Trp Val Tyr Glu Glu Glu Val
1               5

<210> SEQ ID NO 46
<211> LENGTH: 9
<212> TYPE: PRT
<213> ORGANISM: Artificial sequence
<220> FEATURE:
<223> OTHER INFORMATION: DPP9 His 833

<400> SEQUENCE: 46

His Gly Trp Ser Tyr Gly Gly Phe Leu
1               5

<210> SEQ ID NO 47
<211> LENGTH: 8
<212> TYPE: PRT
<213> ORGANISM: Artificial sequence
<220> FEATURE:
<223> OTHER INFORMATION: DPP9 Leu 913 sequence

<400> SEQUENCE: 47

Leu Asp Glu Asn Val His Phe Phe
1               5

<210> SEQ ID NO 48
<211> LENGTH: 6
<212> TYPE: PRT
<213> ORGANISM: Artificial sequence
<220> FEATURE:
<223> OTHER INFORMATION: DPP9 with Glu 944

<400> SEQUENCE: 48

Glu Arg His Ser Ile Arg
1               5

<210> SEQ ID NO 49
<211> LENGTH: 7
<212> TYPE: PRT
<213> ORGANISM: Artificial sequence
<220> FEATURE:
<223> OTHER INFORMATION: DPP9 with Phe 350

<400> SEQUENCE: 49
```

```
Phe Val Ile Gln Glu Glu Phe
1               5

<210> SEQ ID NO 50
<211> LENGTH: 9
<212> TYPE: PRT
<213> ORGANISM: Artificial sequence
<220> FEATURE:
<223> OTHER INFORMATION: DPPIV-like peptide 1

<400> SEQUENCE: 50

His Gly Trp Ser Tyr Gly Gly Phe Leu
1               5

<210> SEQ ID NO 51
<211> LENGTH: 8
<212> TYPE: PRT
<213> ORGANISM: Artificial sequence
<220> FEATURE:
<223> OTHER INFORMATION: DPPIV-like peptide 2

<400> SEQUENCE: 51

Leu Asp Glu Asn Val His Phe Phe
1               5

<210> SEQ ID NO 52
<211> LENGTH: 6
<212> TYPE: PRT
<213> ORGANISM: Artificial sequence
<220> FEATURE:
<223> OTHER INFORMATION: DPPIV-like peptide 3

<400> SEQUENCE: 52

Glu Arg His Ser Ile Arg
1               5

<210> SEQ ID NO 53
<211> LENGTH: 7
<212> TYPE: PRT
<213> ORGANISM: Artificial sequence
<220> FEATURE:
<223> OTHER INFORMATION: DPPIV-like peptide 4

<400> SEQUENCE: 53

Phe Val Ile Gln Glu Glu Phe
1               5

<210> SEQ ID NO 54
<211> LENGTH: 9
<212> TYPE: PRT
<213> ORGANISM: Artificial sequence
<220> FEATURE:
<223> OTHER INFORMATION: DPP9-like peptide 1

<400> SEQUENCE: 54

His Gly Trp Ser Tyr Gly Gly Phe Leu
1               5

<210> SEQ ID NO 55
<211> LENGTH: 8
<212> TYPE: PRT
<213> ORGANISM: Artificial sequence
<220> FEATURE:
<223> OTHER INFORMATION: DPP9-like peptide 2

<400> SEQUENCE: 55

Leu Asp Glu Asn Val His Phe Phe
```

```
-continued
                5

<210> SEQ ID NO 56
<211> LENGTH: 6
<212> TYPE: PRT
<213> ORGANISM: Artificial sequence
<220> FEATURE:
<223> OTHER INFORMATION: DPP9-like peptide 3

<400> SEQUENCE: 56

Glu Arg His Ser Ile Arg
1               5

<210> SEQ ID NO 57
<211> LENGTH: 7
<212> TYPE: PRT
<213> ORGANISM: Artificial sequence
<220> FEATURE:
<223> OTHER INFORMATION: DPP9-like peptide 4

<400> SEQUENCE: 57

Phe Val Ile Gln Glu Glu Phe
1               5
```

The invention claimed is:

1. An isolated nucleic acid molecule that encodes a peptide fragment of the sequence shown in SEQ ID NO:2 wherein said peptide fragment has prolyl dipeptidyl peptidase activity and has the substrate specificity of the sequence shown in SEQ ID NO:2.

2. An isolated nucleic acid molecule that encodes a peptide having prolyl dipeptidyl peptidase activity and the sequence shown in SEQ ID NO:2.

3. A vector comprising the nucleic acid molecule according to claim 1.

4. An isolated cell comprising the vector according to claim 3.

5. An isolated nucleic acid that encodes a fragment of the polypeptide set forth by SEQ ID NO: 2, wherein the fragment has prolyl dipeptidyl peptidase activity.

6. The nucleic acid according to claim 5 that encodes a prolyl dipeptidyl peptidase polypeptide comprising the sequence set forth by SEQ ID NO:2.

7. A composition comprising the nucleic acid molecule according to claim 1.

8. A composition comprising the vector according to claim 3.

* * * * *